(12) United States Patent
Finney

(10) Patent No.: US 12,212,969 B2
(45) Date of Patent: Jan. 28, 2025

(54) AUTOMATIC ASSOCIATION OF A NON-MEDICAL DEVICE WITH A MEDICAL DEVICE

(71) Applicant: MEDTRONIC MINIMED, INC., Northridge, CA (US)

(72) Inventor: Samuel Finney, Los Angeles, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 17/894,725

(22) Filed: Aug. 24, 2022

(65) Prior Publication Data

US 2022/0408267 A1    Dec. 22, 2022

Related U.S. Application Data

(63) Continuation of application No. 16/885,156, filed on May 27, 2020, now abandoned.

(51) Int. Cl.
*H04W 12/50*    (2021.01)
*H04L 9/08*    (2006.01)
(Continued)

(52) U.S. Cl.
CPC .............. *H04W 12/50* (2021.01); *H04L 9/083* (2013.01); *H04L 9/3247* (2013.01); *H04L 9/3271* (2013.01); *H04L 9/3297* (2013.01); *H04L 67/10* (2013.01); *H04W 12/03* (2021.01); *H04W 12/04* (2013.01); *H04W 12/06* (2013.01);
(Continued)

(58) Field of Classification Search
CPC ..... H04W 12/50; H04W 12/03; H04W 12/06; H04W 12/08; H04W 12/71; H04W 76/10; H04L 9/3297; H04L 2209/80
See application file for complete search history.

(56) References Cited

U.S. PATENT DOCUMENTS 4,562,751 A    1/1986 Nason et al.
4,685,903 A    8/1987 Cable et al.
(Continued)

FOREIGN PATENT DOCUMENTS

CN    110868748 A    3/2020
WO    2021242507 A1    12/2021

OTHER PUBLICATIONS

International Search Report and Written Opinion of the International Searching Authority issued in corresponding Application PCT/US2021/031501 mailed Aug. 12, 2021 [MEDTP033WO].
(Continued)

*Primary Examiner* — Robert B Leung
(74) *Attorney, Agent, or Firm* — Weaver Austin Villeneuve & Sampson LLP

(57) ABSTRACT

Techniques disclosed herein relate to automatic association of a non-medical device with a medical device. In some embodiments, the techniques involve accessing a user account provided by a cloud-based service, retrieving first identification information that is stored to the user account and identifies a medical device via the cloud-based service, receiving second identification information from the medical device, and establishing a secure communication link with the medical device based on determining that the second identification information corresponds to or matches the first identification information.

19 Claims, 10 Drawing Sheets

(51) Int. Cl.
| | |
|---|---|
| *H04L 9/32* | (2006.01) |
| *H04L 67/10* | (2022.01) |
| *H04W 12/03* | (2021.01) |
| *H04W 12/04* | (2021.01) |
| *H04W 12/06* | (2021.01) |
| *H04W 12/08* | (2021.01) |
| *H04W 12/71* | (2021.01) |
| *H04W 76/10* | (2018.01) |

(52) U.S. Cl.
CPC .......... *H04W 12/08* (2013.01); *H04W 12/71* (2021.01); *H04W 76/10* (2018.02); *A61M 2205/3561* (2013.01); *A61M 2205/3584* (2013.01); *H04L 2209/80* (2013.01)

(56) References Cited

U.S. PATENT DOCUMENTS

| | | | |
|---|---|---|---|
| 4,755,173 A | 7/1988 | Konopka et al. | |
| 5,080,653 A | 1/1992 | Voss et al. | |
| 5,097,122 A | 3/1992 | Colman et al. | |
| 5,391,250 A | 2/1995 | Cheney, II et al. | |
| 5,485,408 A | 1/1996 | Blomquist | |
| 5,505,709 A | 4/1996 | Funderburk et al. | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | VanAntwerp et al. | |
| 6,017,328 A | 1/2000 | Fischell et al. | |
| 6,088,608 A | 7/2000 | Schulman et al. | |
| 6,119,028 A | 9/2000 | Schulman et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,485,465 B2 | 11/2002 | Moberg et al. | |
| 6,544,212 B2 | 4/2003 | Galley et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,589,229 B1 | 7/2003 | Connelly et al. | |
| 6,591,876 B2 | 7/2003 | Safabash | |
| 6,641,533 B2 | 11/2003 | Causey, III et al. | |
| 6,659,980 B2 | 12/2003 | Moberg et al. | |
| 6,736,797 B1 | 5/2004 | Larsen et al. | |
| 6,740,072 B2 | 5/2004 | Starkweather et al. | |
| 6,749,587 B2 | 6/2004 | Flaherty | |
| 6,752,787 B1 | 6/2004 | Causey, III et al. | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,817,990 B2 | 11/2004 | Yap et al. | |
| 6,827,702 B2 | 12/2004 | Lebel et al. | |
| 6,932,584 B2 | 8/2005 | Gray et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,323,142 B2 | 1/2008 | Pendo et al. | |
| 7,399,277 B2 | 7/2008 | Saidara et al. | |
| 7,402,153 B2 | 7/2008 | Steil et al. | |
| 7,442,186 B2 | 10/2008 | Blomquist | |
| 7,602,310 B2 | 10/2009 | Mann et al. | |
| 7,621,893 B2 | 11/2009 | Moberg et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,474,332 B2 | 7/2013 | Bente, IV et al. | |
| 8,674,288 B2 | 3/2014 | Hanson et al. | |
| 8,979,259 B2 | 3/2015 | Haddock et al. | |
| 9,980,140 B1 | 5/2018 | Spencer et al. | |
| 10,582,444 B1 | 3/2020 | Young et al. | |
| 2007/0123819 A1 | 5/2007 | Mernoe et al. | |
| 2010/0160861 A1 | 6/2010 | Causey, III et al. | |
| 2012/0105346 A1* | 5/2012 | Chen ............... | H04L 63/08 345/173 |
| 2013/0031275 A1* | 1/2013 | Hanes ............. | G06F 3/038 710/5 |
| 2014/0066889 A1 | 3/2014 | Grosman et al. | |
| 2014/0235171 A1* | 8/2014 | Molettiere ....... | A61B 5/486 455/41.2 |
| 2014/0256260 A1* | 9/2014 | Ueda ............... | H04W 76/14 455/41.2 |
| 2014/0273824 A1 | 9/2014 | Fenner et al. | |
| 2017/0359724 A1* | 12/2017 | Katsman ......... | H04L 63/0876 |
| 2018/0084106 A1 | 3/2018 | Li et al. | |
| 2018/0270340 A1* | 9/2018 | Ahmad ............ | H04M 1/72412 |
| 2019/0124701 A1* | 4/2019 | McClellan ....... | G16H 40/63 |
| 2019/0349346 A1 | 11/2019 | Curtis et al. | |
| 2019/0373320 A1* | 12/2019 | Balsamo ......... | G06F 3/0485 |
| 2020/0008057 A1* | 1/2020 | Zhao ............... | H04L 9/0869 |
| 2021/0096881 A1* | 4/2021 | Perlman ......... | G06F 16/252 |
| 2021/0105840 A1 | 4/2021 | Zheng et al. | |
| 2021/0136667 A1 | 5/2021 | Zhou | |
| 2021/0297503 A1* | 9/2021 | Rahn ............... | G06Q 30/0635 |
| 2021/0377726 A1 | 12/2021 | Finney | |

OTHER PUBLICATIONS

U.S. Non-Final Office Action dated May 31, 2022, in U.S. Appl. No. 16/885,156 [MEDTP033US].

EP office action dated Oct. 11, 2023, in EP Application No. 21731334.5 [MEDTP033].

* cited by examiner

AUTOMATIC ASSOCIATION OF A NON-MEDICAL DEVICE WITH A MEDICAL DEVICE

CROSS-REFERENCE TO RELATED APPLICATIONS

This application is a continuation of U.S. patent application Ser. No. 16/885,156, filed May 27, 2020, entitled "METHOD AND SYSTEM FOR AUTOMATICALLY ASSOCIATING A NON-MEDICAL DEVICE WITH A MEDICAL DEVICE," which is herein incorporated by reference in its entirety for all purposes.

TECHNICAL FIELD

Embodiments disclosed herein relate generally to the medical arts and, more specifically, to automatic association of a non-medical device with a medical device.

BACKGROUND

Wireless devices, such as cellular telephones, mobile computers, personal digital assistants, digital media players, portable video game devices, and the like, and related wireless communication techniques and protocols have become ubiquitous in modern society. More recently, portable medical devices having wireless data communication capabilities are becoming increasingly popular, especially for patients that have conditions that must be monitored on a continuous or frequent basis. For example, diabetics are usually required to modify and monitor their daily lifestyle to keep their body in balance, in particular, their blood glucose ("BG") levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly. Diabetics may utilize wireless medical devices that are deployed in a network environment in a manner that facilitates data communication between two or more separate devices.

In the past, on-body medical devices, such as fluid infusion device (or infusion pump) and sensing arrangement (e.g., continuous glucose sensors), could be controlled using a custom controller device (CCD). Today, there is a growing trend towards controlling personal medical devices, such as insulin infusion devices that are worn by a patient, using a non-medical device such as a patient's smart phone, laptop or tablet. On-body medical devices can now be communicated with and controlled using a non-medical smart device (e.g., smartphone, tablet). One advantage of this approach is that it can eliminate the need for a patient to possess and use another distinct control device. This can make the cost of ownership lower. In addition, patients can be discreet in managing their disease, and use a familiar user interface and form-factor which shortens the learning curve. This can also provide connectivity to back end systems (e.g., cloud-based systems) that are used to monitor patients and control delivery of medication to a patient. Non-medical smart devices can upload data for analysis by health care providers (HCPs) and AI-based systems. Non-medical smart devices can also receive regular updates to therapy management software. For instance, these updates can update medical control application software (or key parameters thereof) to customize and improve therapy. Connectivity also provides the means to alert caregivers and HCPs in emergency situations when concerning trends are present. A medical control application can also use health related data from the non-medical smart device and other apps/systems to improve therapy for the patient.

A number of insulin pump systems are designed to deliver accurate and measured doses of insulin via infusion sets (an infusion set delivers the insulin through a small diameter tube that terminates at a cannula inserted under the patient's skin). In lieu of a syringe, the patient can simply activate the insulin pump to administer an insulin bolus as needed, for example, in response to the patient's current BG level. A patient can measure his BG level using a BG measurement device, such as a test strip meter, a continuous glucose measurement system, or the like. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device. A continuous glucose monitoring system can monitor the patient's sensor glucose (SG) level (e.g., subcutaneous tissue glucose level) in real-time. This allows delivery of insulin to be calculated in real-time with dosage calculated in a software algorithm based on measured sensor glucose level, or a closed-loop algorithm.

The insulin pump, continuous glucose monitoring (CGM) device, and other devices, such as a smartphone and a Blood Glucose Monitor (BGM), can be different parts of an insulin infusion system. The various devices that are part of the insulin infusion system can form a wireless body area network that can be used, for example, to exchange monitor and therapy (control) data among multiple medical devices that are either worn on or near a patient's body. For instance, therapy data such as measured glucose values (SG values) and therapy settings (parameters for bolus delivery) can be transferred wirelessly among devices within the body area network. Insulin pumps and CGM devices may also be configured to communicate with remote control devices, monitoring or display devices, BG meters, and other devices associated with such an infusion system. For example, a CGM sensor may include or cooperate with a wireless radio frequency ("RF") transmitter that communicates with other devices that are part of an infusion system such as a handheld remote control (also called a command control device (CCD)) that communicates with the infusion pump device using wireless communication technologies such as classical Bluetooth® (BT) or Bluetooth Low Energy® (BLE) technologies.

BRIEF SUMMARY

Techniques disclosed herein relate to automatic association of a non-medical device with a medical device. The techniques may be practiced using a processor-implemented method; a system comprising one or more processors and one or more processor-readable media; and one or more non-transitory processor-readable media.

According to certain embodiments, the techniques involve accessing a user account provided by a cloud-based service; retrieving, via the cloud-based service, first identification information stored to the user account and identifying a medical device; receiving, from the medical device, second identification information; and based on determining that the second identification information corresponds to or matches the first identification information, establishing a secure communication link with the medical device.

The following detailed description together with the accompanying drawings will provide a better understanding of the nature and advantages of the present invention.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
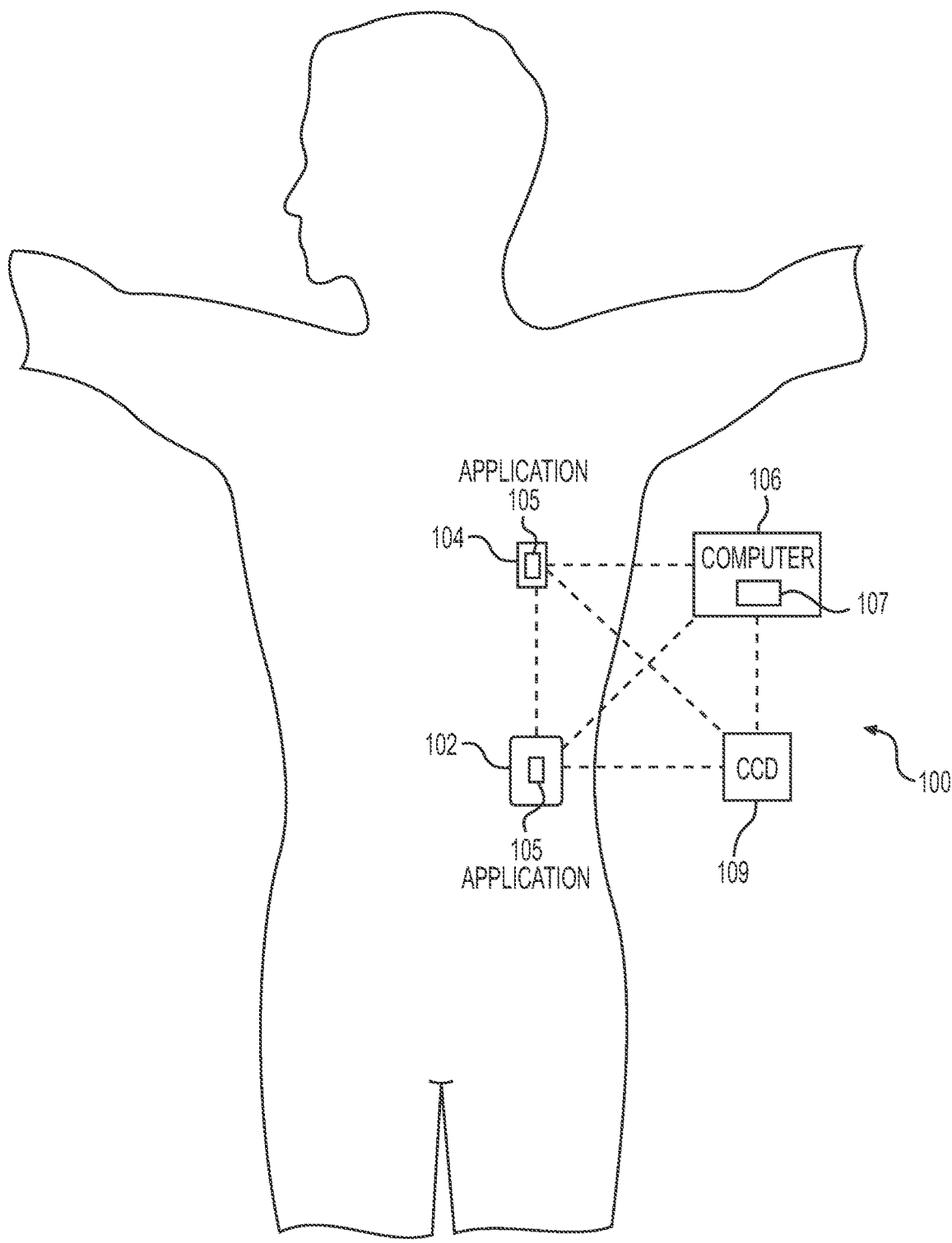
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software, firmware, or processor-readable instructions, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

Exemplary embodiments of the subject matter described herein are implemented in conjunction with medical devices, such as portable electronic medical devices. Although many different applications are possible, the following description focuses on embodiments that incorporate an insulin infusion device (or insulin pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to linearly displace a plunger (or stopper) of a fluid reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop or automatic operating mode, dosage commands may be generated based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Wireless technology may be used in medical devices (MDs) to monitor therapy, configure therapy, perform diagnostics, and analyze health data. This technology can be used in conjunction with non-medical devices (NMDs), such as, patient-owned smartphones or other general-purpose computing devices, to enhance the user experience and provide additional device capabilities. For instance, many medical devices can use a non-medical device, such as a smartphone, as a conduit for delivery of data that is sent from a remote server system over a network (e.g., from a cloud-based computing platform over the Internet), or vice-versa. In these cases, the medical device can communicate with a non-medical device over a short-range communication link, such as, for example, over a Bluetooth® (BT) or Bluetooth® Low Energy (BLE) communication link, and the non-medical device can then communicate with a back-end server system over longer-range communication network(s).

Smart devices (e.g., smartphones, smart assistants (including smart speakers or other devices), watches, other wearable devices, etc.) are devices that are available to the general public and have other uses beyond medical applications. Using such non-medical devices as part of a medical device system can provide a number of advantages. While using non-medical devices in conjunction with medical device can provide a number of advantages, one risk from the perspective of medical device manufacturers is that a smartphone or other smart devices are a relatively open platform and not as controllable as a medical device. In addition, the process of associating or pairing a medical device with other non-medical devices can be relatively complicated and require a good amount of manual configuration by the user (e.g., patient or health care provider). The process of associating a medical device with a patient-owned device can be burdensome to the patient. For example, a user may have to input commands into their non-medical device and/or medical device to initiate a pairing process to associate their medical device with the non-medical device, and vice-versa. Then, to pair with the non-medical device, the medical device searches for identifying information (e.g., a serial number or other identifying number that is broadcast by the non-medical device (along other metadata such as filtering IDs that help medical device to identify other devices that it should not pair with). In some systems, the roles may be reversed such that the non-medical device may search for identifying information broadcast by the medical device, or one medical device may search for identifying information broadcast by another medical device. In some instances, the user must then manually inspect and verify the identifying information on one or both devices to confirm that the correct devices were paired. This process is also prone to errors.

Furthermore, this pairing process can become more burdensome as the number of medical and non-medical devices in a crowded environment (e.g., a clinic setting) increases. For instance, it can become difficult to identify which non-medical device a particular medical device is trying to pair with when there are a large number of non-medical devices within communication range of the medical device (e.g., in an environment that is crowded with many non-medical devices). A patient might inadvertently associate their personal device with the wrong medical device. These problems become more acute when medical devices are replaced more frequently, requiring frequent repetition of the association process.

It is desirable to provide a medical device system, such as an insulin infusion system, that can provide patients with a reliable means of automating this process such that a patient's personal, non-medical device can automatically associate with and connect to a medical device prescribed to that patient, or vice-versa.

To address these issues a method and system are provided for authorizing a first device to automatically communicate with a second device. One of the first device and the second device is a particular medical device for a patient, and the other one of the first device and the second device is a particular non-medical device associated with the patient. For example, in one embodiment, the first device is the particular medical device and the second device is the particular non-medical client device that is configured to execute a medical control application that controls and/or monitors a particular medical device. In another embodiment, the second device is the particular medical device, and the first device is the particular non-medical client device that is configured to execute a medical control application that controls the particular medical device.

In one embodiment, a method and system are provided for authorizing a first device to communicate with a second device. One of the first device and the second device is a particular medical device for a patient, and the other one of the first device and the second device is a particular non-medical device associated with the patient. For example, in one embodiment, the first device is the particular medical device and the second device is the particular non-medical client device that is configured to execute a medical control application that controls particular medical device. In another embodiment, the second device is the particular medical device, and the first device is the particular non-medical client device that is configured to execute a medical control application that controls the particular medical device.

Prior to the second device being authorized to communicate with the first device, first identification information that identifies the second device can be provided to the first device via a cloud-based computing system. The first device can be pre-populated with the first identification information for the second device via the cloud-based computing system prior to the second device being authorized to communicate with the first device. For instance, in one embodiment, the cloud-based computing system can identify the second device associated with the patient at and retrieve first identification information for the second device, and store the first identification information in an account for the patient. When the account is accessed by the patient, prior to the second device being authorized to communicate with the first device, the first identification information for the second device can be retrieved and sent to the first device of the patient to prepopulate the first device with the first identification information for the second device.

The first identification information for the second device is used by the first device to identify the second device and automatically associate with the second device so that the first device can securely communicate over the secure communication link between the second device and the first device without additional authentication processing being performed by the first device and, in some implementations, without a user having to perform manual configuration steps at the second device or the first device. The first identification information can be, for example, pairing information that is used to automatically pair the second device with the first device. Alternatively, the first identification information can be a unique identification information set (described herein) for the second device. For instance, this unique identification information set can include one or more of: a device serial number associated with the second device; a numeric identifier associated with the second device; a cryptographic public signature verification key with a corresponding unique private signing key that was previously stored in the second device; or a cryptographic private payload decryption key with a corresponding unique public encryption key that was previously stored at the second device.

When the second device is prepared for use, it can broadcast second identification information. When the first device determines that the second identification information corresponds to or matches the first identification information stored at the first device, the first device can automatically establish a secure communication link with the second device and the first device. To explain further, in some cases correspondence is enough, whereas in other cases a match is required (e.g., the information stored in both devices is identical). For identification schemes using public/private key cryptography or other measures, the information might be different but mathematically related. In one embodiment, the second device can broadcast an association message that comprises the second identification information, and the first device, upon receiving the association message, can then process the second identification information to automatically establish the secure communication link between the second device and the first device. For instance, the first device can compare the second identification information from the association message to the first identification information stored at the first device, and if the second identification information from the association message corresponds to or matches the first identification information stored at the first device, the first device can automatically associate the first device with the second device and establish the secure communication link between the second device and the first device. In one implementation, the first device can send another request (with appropriate authentication information or first identification information) to the second device, which can process the authentication information or the first identification information to determine whether that the authentication information or the first identification information is valid. When the authentication information or the first identification information is determined to be valid, and the second device is within a threshold distance from the first device, the second device can automatically associate with the first device by establishing at least one shared security attribute between the first device and the second device to support secure communications over the secure communication link between that first device and the second device. In other implementations, establishing a connection may involve one or more back-and-forth message exchanges, depending on the wireless technology used and the authentication information or the first identification information involved.

The second identification information broadcast in each association message can comprise at least one of: a device serial number or other numeric identifier; a deterministic function of a device serial number or other numeric identifier; a random number; a timestamp or other non-recurring value; a cryptographic signature; the device serial number or other numeric identifier encrypted with a cryptographic key; the deterministic function of a device serial number or other numeric identifier encrypted with the cryptographic key; the random number encrypted with the cryptographic key; the timestamp or other non-recurring value encrypted with the cryptographic key; the device serial number or other numeric identifier encrypted with the cryptographic key and accompanied by a cryptographic signature; the deterministic function of a device serial number or other numeric identifier encrypted with the cryptographic key and accompanied by the cryptographic signature; the random number encrypted with the cryptographic key and accompanied by the cryptographic signature; and the timestamp or other non-recurring value encrypted with the cryptographic key and accompanied by the cryptographic signature In one embodiment, the cloud-based service provides the first device with wireless traffic encryption keys in addition to keying material used for identification and authentication. In one embodiment, the first device and the second device are required to complete a cryptographic challenge-response handshake process before a connection is established between the first device and the second device.

Pre-configuring patient devices with information needed for association with medical devices has several benefits, including, but not limited to, enhanced security and reliability, reduced user burden, reduced risk of user error, and a seamless user experience. Reducing the risk of user error and enhancing device security may ease the regulatory approval process for manufacturers of medical devices and mitigate risk of patient harm. Improvements in the usability of medical devices can help reduce user burden and provide an easy, seamless user experience.

Turning now to FIG. 1, one exemplary embodiment of an infusion system 100 includes, without limitation, a fluid infusion device (or infusion pump) 102, a sensing arrangement 104, a computer 106 and a command control device (CCD) 109. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 109 and/or the computer 106. For example, the infusion device 102, the CCD 109 and/or the computer 106 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 109 and/or the computer 106 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 109, and/or the computer 106 includes a transmitter, a receiver, and/or other transceiver electronics that allow for communication with other components of the infusion system 100, so that the sensing arrangement 104 may transmit sensor data or monitor data to one or more of the infusion device 102, the CCD 109 and/or the computer 106.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 109. In such embodiments, the sensing arrangement 104 may be configured to receive a biological sample, analyte, or the like, to measure a condition of the user.

In some embodiments, the CCD 109 and/or the computer 106 may include electronics and other components configured to perform processing, delivery routine storage, and to control the infusion device 102 in a manner that is influenced by sensor data measured by and/or received from the sensing arrangement 104. By including control functions in the CCD 109 and/or the computer 106, the infusion device 102 may be made with more simplified electronics. However, in other embodiments, the infusion device 102 may include all control functions, and may operate without the CCD 109 and/or the computer 106. In various embodiments, the CCD 109 may be a portable electronic device. In addition, in various embodiments, the infusion device 102 and/or the sensing arrangement 104 may be configured to transmit data to the CCD 109 and/or the computer 106 for display or processing of the data by the CCD 109 and/or the computer 106.

In some embodiments, the CCD 109 and/or the computer 106 may be non-medical devices that provide information to the user that facilitates the user's subsequent use of the infusion device 102 or allow the user to control infusion device 102. For example, the CCD 109 may provide information to the user to allow the user to determine the rate or dose of medication to be administered into the user's body. In other embodiments, the CCD 109 may provide information to the infusion device 102 to autonomously control the rate or dose of medication administered into the body of the user. In some embodiments, the sensing arrangement 104 may be integrated into the CCD 109. Such embodiments may allow the user to monitor a condition by providing, for example, a sample of his or her blood to the sensing arrangement 104 to assess his or her condition. In some embodiments, the sensing arrangement 104 and the CCD 109 may be used for determining glucose levels in the blood and/or body fluids of the user without the use of, or necessity of, a wire or cable connection between the infusion device 102 and the sensing arrangement 104 and/or the CCD 109.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
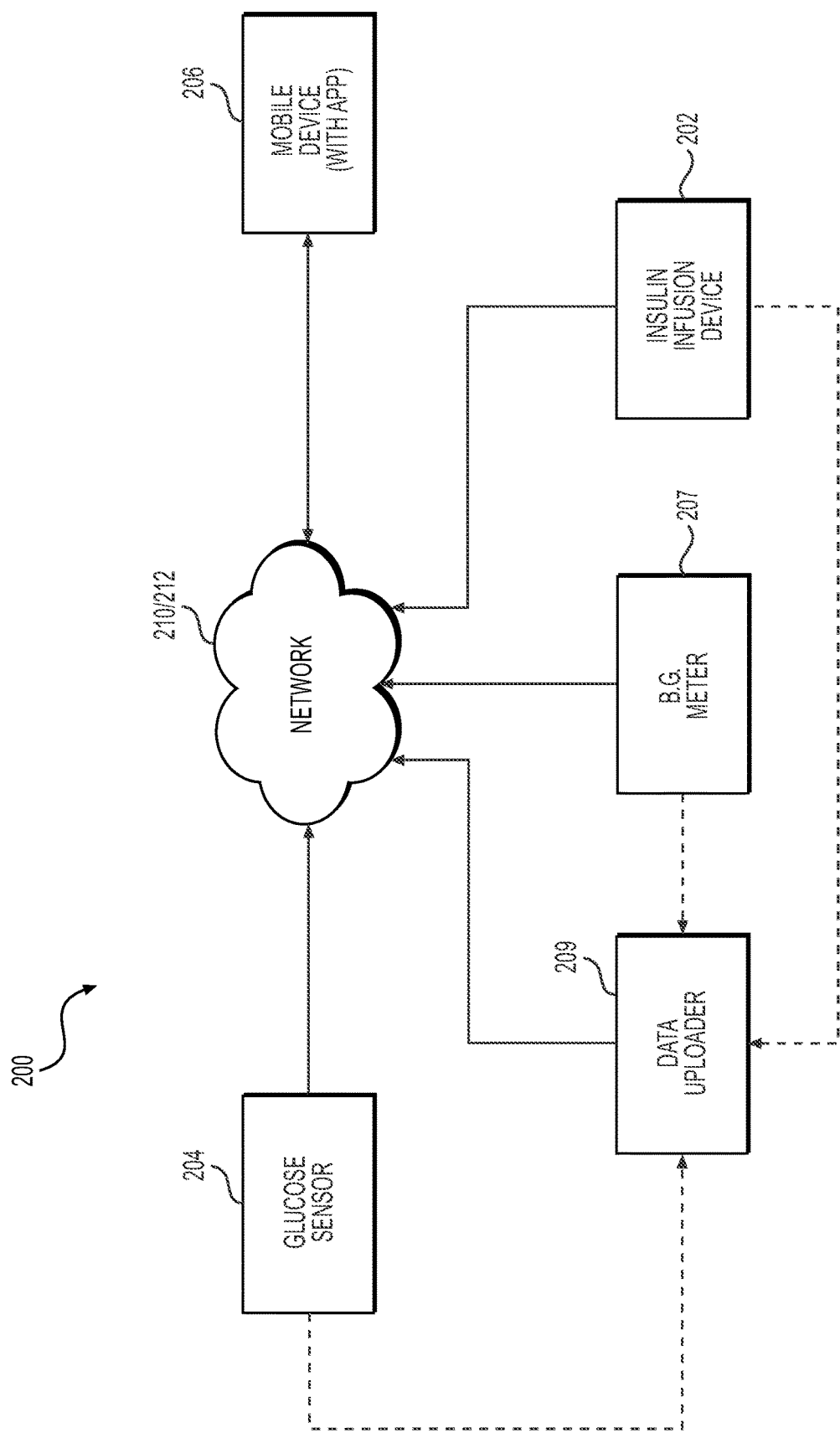
FIG. 2 is a simplified block diagram representation of an exemplary embodiment of a communication system.

FIG. 2 is a simplified block diagram representation of an exemplary embodiment of a communication system 200 that is suitably configured to support the techniques and methodologies described in more detail below. The system 200 supports users of insulin infusion devices, and performs various techniques and methods to help users (patients, caregivers, healthcare providers, parents, etc.) manage the use of insulin infusion devices. It should be appreciated that FIG. 2 depicts one possible implementation of a communication system, and that other arrangements, architectures, and deployments can be provided if so desired. The system 200 (which has been simplified for purposes of illustration) generally includes or cooperates with the following components, without limitation: an insulin infusion device 202; a continuous glucose sensor 204; a mobile device 206; an optional blood glucose meter 207; and an optional data uploader 209. The mobile device 206 is a client device that is owned or operated by the user, i.e., a diabetic patient. The insulin infusion device 202, the glucose sensor 204, and the blood glucose meter 207 are components of an insulin infusion system that is used by the patient to treat diabetes. The system 200 may also include or cooperate with the optional data uploader component 209.

The various components of the system 200 can be used to collect and analyze input data for the patient that can originate from various sources, including an insulin infusion device, a glucose sensor or meter, a mobile device operated by a user of the insulin infusion device, or other components or computing devices that are compatible with the system, such as a data uploader. These and other alternative arrangements are contemplated by this disclosure. To this end, some embodiments of the system may include additional devices and components that serve as data sources, data processing units, etc. For example, the system may include any or all of the following elements, without limitation: computer devices or systems; patient monitors; healthcare provider systems; data communication devices; and the like. It should be appreciated that the insulin infusion device 202 can be an optional component in some applications (for example, for Type 2 diabetes patients). For such applications, another diabetes management device and/or the mobile device 206 can function in an equivalent manner to support the system 200.

At a minimum, the mobile device 206 is communicatively coupled to a network 210/212. In certain embodiments, the insulin infusion device 202, the blood glucose meter 207, and/or the continuous glucose sensor 204 are also communicatively coupled to the network 210/212 to facilitate the uploading of relevant data to a remote server system (not illustrated). Alternatively, or additionally, the insulin infusion device 202, the blood glucose meter 207, and the continuous glucose sensor 204 provide relevant data to the data uploader component 209, which in turn uploads the data to other systems (not illustrated) via the network 210/212.

FIG. 2 depicts the network 210/212 in a simplified manner. In practice, the system 200 may cooperate with and leverage any number of wireless and any number of wired data communication networks maintained or operated by various entities and providers. Accordingly, communication between the various components of the system 200 may involve multiple network links and different data communication protocols. In this regard, the network 210/212 can include or cooperate with any of the following, without limitation: a local area network; a wide area network; the Internet; a personal area network; a cellular communication network; a satellite communication network; a video services or television broadcasting network; a network onboard a vehicle; or the like. In addition, the various components can also communicate directly with each other using NFMI radio communications; NFeMI radio communications, BLE® communications, classical Bluetooth® (BT) communications, WLAN (or "Wi-Fi") communications, or indirectly with each other using WLAN or cellular communications, as will be described below. The components of the system may be suitably configured to support a variety of wireless and wired data communication protocols, technologies, and techniques as needed for compatibility with the network 210/212.

The mobile device 206 can be realized using a variety of different device platforms. For example, the mobile device 206 can be implemented as any of the following, without limitation: a cellular telephone or smartphone; a portable computer (e.g., a laptop, a tablet, or a netbook computer); a portable media player; a portable video game device; a portable medical device; a navigation device such as a global positioning system (GPS) device; a wearable computing device; an electronic toy or game; etc. In accordance with certain exemplary embodiments, the mobile device 206 supported by the system 200 is implemented as a computer-based or processor-based component. For simplicity and ease of illustration, FIG. 2 depicts only one mobile device 206. In practice, however, the system 200 is suitably configured to support a plurality of mobile devices 206, where the patient or user owns or operates at least one of the supported mobile devices 206. An exemplary embodiment of a device suitable for implementing the mobile device 206 is described below with reference to FIG. 3.

The remainder of this description assumes that the mobile device 206 is a smartphone used by the particular patient. To this end, the configuration and general functionality of the mobile device 206 can be substantially consistent with conventional smartphone design. In this regard, a suitably designed mobile app is installed on the mobile device 206 to allow the patient to receive, view, and interact with messages and notifications provided by the system (e.g., a medical control application that controls and/or monitors a particular medical device such as any of devices 202, 204, 207, and/or 209). The mobile app installed on the mobile device 206 can also be utilized to provide relevant data to other systems (not illustrated) for storage and analysis. For example, the mobile app can manage and upload the following information, without limitation: calendar data (time of day, day of the week, month, season, etc.); user profile data; GPS data that indicates the geographic position of the mobile device 206; map or navigation data associated with operation of the mobile device 206; user-entered meal consumption, food content, and/or food ingredient data; user-entered carbohydrate data; user-entered exercise related data; user-entered medication related data; user response data associated with the receipt of glycemic insight messages; user feedback related to glycemic insight messages; accelerometer data; contacts list information; web browser data; consumer purchasing data; and the like.

In certain embodiments, the insulin infusion device 202 is a portable patient-worn or patient-carried component that is operated to deliver insulin into the body of the patient via, for example, an infusion set. In accordance with certain exemplary embodiments, each insulin infusion device 202 supported by the system 200 is implemented as a computer-based or processor-based component. For simplicity and ease of illustration, FIG. 2 depicts only one insulin infusion device 202. In practice, however, the system 200 is suitably configured to support a plurality of insulin infusion device 202, wherein each patient or user owns or operates at least one of the insulin infusion devices 202. An exemplary embodiment of a device suitable for implementing the insulin infusion device 202 is described below with reference to FIG. 3.

The system 200 obtains input data from one or more sources, which may include various diabetes management devices (an insulin infusion device, a continuous glucose monitoring device, a glucose sensor, a monitor device, or the like). In this regard, the insulin infusion device 202 represents a source of input data for the system 200. In certain embodiments, the insulin infusion device 202 provides data that is associated with its operation, status, insulin delivery events, and the like. As mentioned previously, relevant data generated or collected by the insulin infusion device 202 can be transmitted directly or indirectly to other components of the system including the data uploader component 209, depending on the particular implementation of the system 200. The particular type of data provided by the insulin infusion device 202 is described in more detail below.

The patient or user can own or operate the blood glucose meter 207. The blood glucose meter 207 is configured to measure the blood glucose level of a user by analyzing a blood sample. For example, the blood glucose meter 207 may include a receptacle for receiving a blood sample test strip. In this regard, the user inserts a test strip into the blood glucose meter 207, which analyzes the sample and displays a blood glucose level corresponding to the test strip sample. The blood glucose meter 207 may be configured to communicate the measured blood glucose level to the insulin infusion device 202 for storage and processing, to the mobile device 206, or to the data uploader component 209. In some scenarios, the patient is responsible for entering each blood glucose measurement into the insulin infusion device 202. Ultimately, the measured blood glucose data can be provided to any components of the system for analysis.

The glucose sensor 204 can be owned or operated by the patient or user. The glucose sensor 204 is suitably configured to measure a glucose level (interstitial) of the patient in real time. The glucose sensor 204 may include a wireless transmitter that facilitates transmission of the sensor glucose data to other devices, such as the insulin infusion device 202 or the data uploader component 209 or other components of the system, where the sensor glucose data can be received for further processing.

Depending on the particular embodiment and application, the system 200 can include or cooperate with other devices, systems, and sources of input data. Devices within the system 200 may be configured to support the transmission of data to various external devices, such as, without limitation: a stationary monitor device, such as a bedside monitor or a piece of hospital monitoring equipment; a portable computer, such as a laptop PC, a palmtop PC, or a tablet PC; a stationary computer, such as a desktop PC; a personal digital assistant, which may also be a portable email device; one or more additional computing devices or databases; or the like. The above list of possible external devices is not exhaustive, and an implementation of the system 200 can be designed to accommodate communication with other systems, equipment, computing devices, components, and elements that are external to the system 200. For example, in certain embodiments the system 200 includes one or more sources of contextual information or data, which may include, without limitation: activity tracker devices; meal logging devices or apps; mood tracking devices or apps; and the like.

The system 200 includes a local infusion system having one or more local devices configured to wirelessly communicate with each other. This description may refer to the local infusion system as a "personal area network" or a "body area network" of its constituent devices. These local devices may be configured to transmit and receive local communications within the local infusion system, where such local communications are transmitted and received in accordance with one or more specified local data communication protocols. For example, local communications may be exchanged between local devices using one or more wireless data communication protocols (which may leverage RF, infrared, magnetic induction, or other wireless techniques) and/or using one or more wired data communication protocols. Thus, one or more of the local devices can be considered to be a wireless medical device in the context of this description. The local infusion system may be flexibly configured such that any given local device can communicate with any other local device, and a communication link or path between two local devices may be unidirectional or bidirectional. FIG. 2 depicts an exemplary embodiment where each communication link or path is bidirectional (represented by double headed arrows).

Moreover, the local devices in the local infusion system may be capable of communication (unidirectional or bidirectional) with one or more "external" devices that are not considered to be part of the local infusion system. The manner in which a given local device within the local infusion system communicates with a given external device may vary depending upon the particular configuration of the system 200, the characteristics of the local device, and the characteristics of the external device. For example, data may be routed between the local infusion system and an external device using one data communication network, using a plurality of data communication networks, using a direct wireless or wired connection, or the like As mentioned above, the system 200 includes or cooperates with computer-based and/or processor-based components having suitably configured hardware and software written to perform the functions and methods needed to support the features described herein. For example, the insulin infusion device 202, the mobile device 206, the blood glucose meter 207 and the data uploader component 209 can be realized as a computer-based or an electronic processor-based component. An exemplary embodiment of a computer-based or processor-based device suitable for implementing the various components of the system will described below with reference to FIG. 3.

Figure 3:
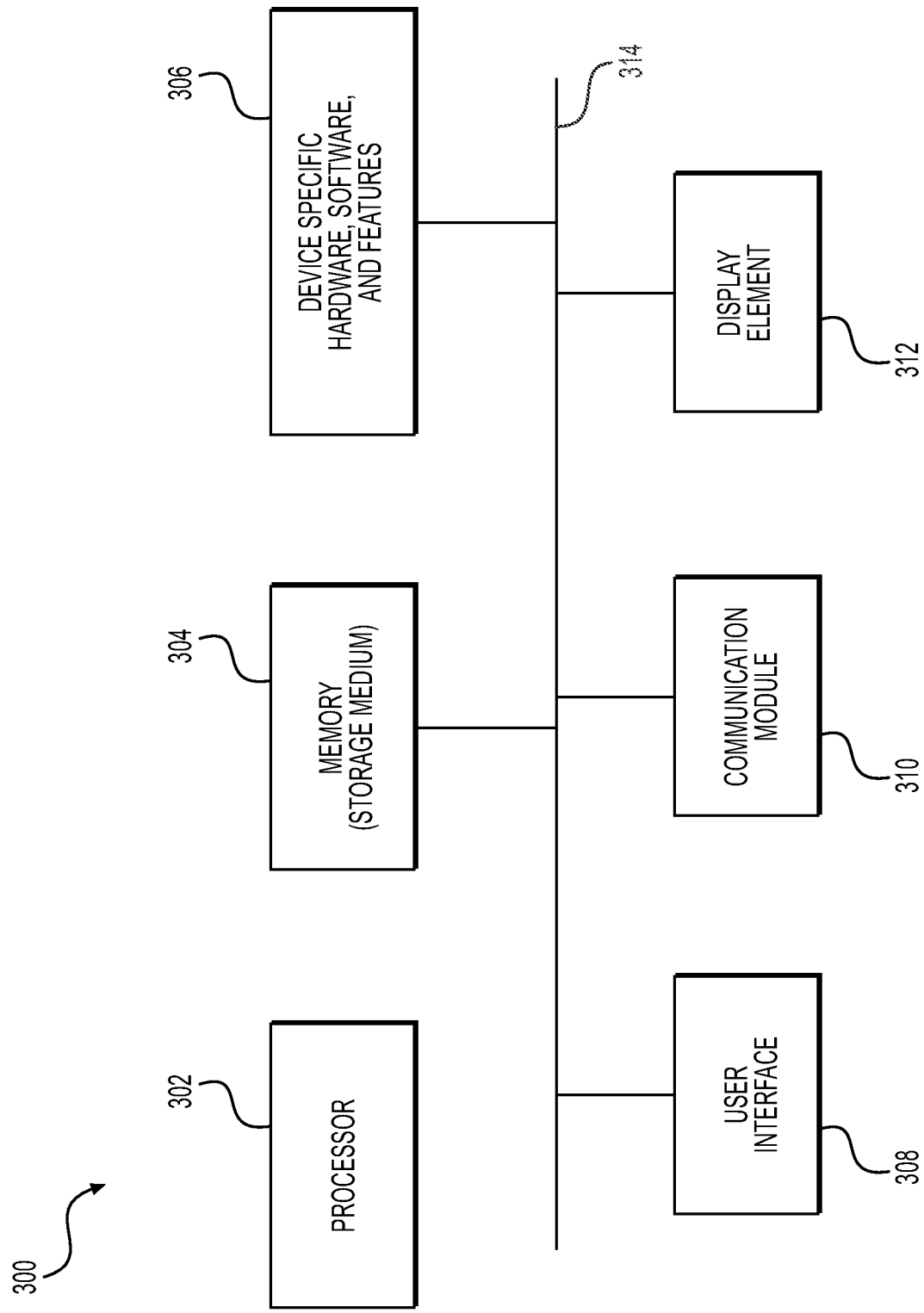
FIG. 3 is a simplified block diagram representation of an exemplary embodiment of a computer-based or processor-based device in accordance with the disclosed embodiments.

FIG. 3 is a simplified block diagram representation of an exemplary embodiment of a computer-based or processor-based device 300 that is suitable for deployment in the system shown in FIGS. 1 and 2. In this regard, each of the devices or components that are described above with reference to FIGS. 1-2 can be realized as a computer-based or processor-based device/component 300. In addition, each of the devices or components that are described below with reference to FIGS. 4 and 5 can also be realized as a computer-based or processor-based device/component 300.

The illustrated embodiment of the device 300 is intended to be a high-level and generic representation of one suitable platform. In this regard, any of the computer-based or processor-based components of the system 200 can utilize the architecture of the device 300. The illustrated embodiment of the device 300 generally includes, without limitation: at least one processor 302; a suitable amount of memory 304; device-specific hardware, software, firmware, and/or features 306; a user interface 308; a communication module 310; and a display element 311. Of course, an implementation of the device 300 may include additional elements, components, modules, and functionality configured to support various features that are unrelated to the subject matter described here. For example, the device 300 may include certain features and elements to support conventional functions that might be related to the particular implementation and deployment of the device 300. In practice, the elements of the device 300 may be coupled together via a bus or any suitable interconnection architecture 301.

The processor 302 may be implemented or performed with a general-purpose processor, a content addressable memory, a digital signal processor, an application specific integrated circuit, a field programmable gate array, any suitable programmable logic device, discrete gate or transistor logic, discrete hardware components, or any combination designed to perform the functions described here. Moreover, the processor 302 may be implemented as a combination of computing devices, e.g., a combination of a digital signal processor and a microprocessor, a plurality of microprocessors, one or more microprocessors in conjunction with a digital signal processor core, or any other such configuration.

The memory 304 may be realized as RAM memory, flash memory, EPROM memory, EEPROM memory, registers, a hard disk, a removable disk, a CD-ROM, or any other form of storage medium known in the art. In this regard, the memory 304 can be coupled to the processor 302 such that the processor 302 can read information from, and write information to, the memory 304. In the alternative, the memory 304 may be integral to the processor 302. As an example, the processor 302 and the memory 304 may reside in an ASIC. At least a portion of the memory 304 can be realized as a computer storage medium, e.g., a tangible computer-readable medium having computer-executable instructions stored thereon. The computer-executable instructions, when read and executed by the processor 302, cause the device 300 to perform certain tasks, operations, functions, and processes that are specific to the particular embodiment. In this regard, the memory 304 may represent one suitable implementation of such computer-readable media. Alternatively, or additionally, the device 300 could receive and cooperate with computer-readable media (not separately shown) that is realized as a portable or mobile component or platform, e.g., a portable hard drive, a USB flash drive, an optical disc, or the like.

The device-specific hardware, software, firmware, and features 306 may vary from one embodiment of the device 300 to another. For example, the device-specific hardware, software, firmware, and features 306 will support: smartphone functions and features when the device 300 is realized as a mobile telephone; conventional personal computer functions and features if the device 300 is realized as a laptop or tablet computer; insulin pump operations when the device 300 is realized as an insulin infusion device; etc. In practice, certain portions or aspects of the device-specific hardware, software, firmware, and features 306 may be implemented in one or more of the other blocks depicted in FIGS. 3 and 4.

The user interface 308 may include or cooperate with various features to allow a user to interact with the device 300. Accordingly, the user interface 308 may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 300. The user interface 308 may include one or more graphical user interface (GUI) control elements that enable a user to manipulate or otherwise interact with an application via the display element 311.

The communication module 310 facilitates data communication between the device 300 and other components as needed during the operation of the device 300. In the context of this description, the communication module 310 can be employed to transmit or stream device-related control data, patient-related data, device-related status or operational data, glycemic insight messages and notifications, and the like. It should be appreciated that the particular configuration and functionality of the communication module 310 can vary depending on the hardware platform and specific implementation of the device 300. Accordingly, the communication module 310 is utilized to obtain input data from various sources, and to send output data to other components or devices that are described above with reference to FIGS. 1 and 2. In practice, an embodiment of the device 300 may support wireless data communication and/or wired data communication, using various data communication protocols. For example, the communication module 310 could support one or more wireless data communication protocols, techniques, or methodologies, including, without limitation: RF; IrDA (infrared); Bluetooth®; ZigBee® (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication module 310 could support one or more wired/cabled data communication protocols, including, without limitation: Ethernet; powerline; home network communication protocols; USB; IEEE 2394 (Firewire); hospital network communication protocols; and proprietary data communication protocols. In one particular implementation, the communication module 310 includes a far-field communication module and a body area network communication module, and a controller (not illustrated).

The far-field communication module includes various far-field communication interfaces that can be used to communicate electromagnetic signals to other devices that are part of a body area network. In this non-limiting example, various far-field communication interfaces can include, but are not limited to, a Bluetooth low energy (BLE®) communication interface, a classical Bluetooth® (BT) communication interface, a wireless local area network (WLAN) communication interface (e.g., a Wi-Fi interface), and a cellular communication interface. The above-mentioned communication interfaces can comply with any known standards. For example, the BLE® communication interface can communicate in compliance with any Bluetooth® release (e.g., versions 1.0 through 5.1), and any physical (PHY) layer specifications defined therein. For instance, Bluetooth® 5.0 includes three PHY layer variations called LE 1M, LE 2M and LE Coded. Each PHY variant has its own particular characteristics and was designed with specific aims in mind. As another non-limiting example, the BLE® communication interface can communicate in compliance with a Bluetooth® mesh networking protocol (defined in Mesh Profile Specification and Mesh Model Specification which was adopted on Jul. 13, 2017). The Bluetooth® mesh networking protocol is a protocol based upon Bluetooth Low Energy® that allows for many-to-many communication over Bluetooth® radio.

When a signal from a far-field communication interface is transmitted by an antenna, it is attenuated over distance to the point that the signal cannot be effectively detected. This is called far-field transmission, and works well if the signal needs to be transmitted over a long distance. However, far-field communication interfaces can have problems if the wireless communication needs to be very low power and confines to a fairly short distance near body areas. Improper placement of devices close to a human body may result in a detuned antenna input impedance, reduced antenna efficiency, and distorted antenna radiation pattern. Penetration of electromagnetic signals generated by far-field communication interfaces into the human body is another problem because electromagnetic signals can be quickly absorbed and greatly attenuated due to the very conductive body tissues. In addition, interference can be very high due to coexistence of multiple far-field communication interfaces (e.g., BT, BLE®, Wi-Fi, and ZigBee®) that operate in the same frequency band. Power consumption can also limit continuous operation. Lastly, far-field communication interface can present potential security problems because electromagnetic signals can be intercepted and decrypted after propagating into free space.

On the other hand, the body area network communication module includes various near-field communication interfaces that can be used to communicate magnetic signals to other devices that are part of a body area network. In this non-limiting example, various near-field communication interfaces can include, but are not limited to, a near field magnetic inductive (NFMI) radio communication interface, a near-field electromagnetic induction (NFeMI) radio communication interface (not illustrated), a near field communication (NFC) interface, an RFID high-frequency (HF) communication interface, and one or more low power wide area network (LPWAN) communication interfaces. A near-field communication interface can provide a more reliable, a more secure, and a much lower power radio link within, on, and in the immediate proximity of a human body.

For example, NFMI is a short-range wireless technology that communicates using a tightly coupled magnetic field among devices. NFMI enables human body friendly, reliable, secure, and power efficient wireless communication. As used herein, the term "Near-Field Magnetic Induction (NFMI) radio communication system" can refer to a short range wireless physical layer that communicates by coupling a tight, low-power, non-propagating magnetic field between devices. A transmitter coil in one device can modulate a magnetic field which is measured by a receiver coil in another device. To explain further, in NFMI-based communication systems, a modulated signal that is sent out from a transmitter coil is in the form of a magnetic field. This magnetic field induces voltage on the receiving coil, which in turn will be measured by an NFMI receiver. NFMI radio communication systems differ from other wireless communications in that most conventional wireless RF systems use an antenna to generate, transmit, and propagate an electromagnetic wave, where all of the transmission energy is designed to radiate into free space. This type of transmission is referred to as "far-field." NFMI systems are designed to contain transmission energy within the localized magnetic field. This magnetic field energy resonates around the communication system, but does not radiate into free space. To explain further, the power density of NFMI signals attenuate at a rate inversely proportional to the distance to the sixth power compared to the second power for Bluetooth® signals. This means for the same distance, the power density of NFMI signals is 10000 times weaker than Bluetooth® signals provided that both transmitting power are equal. This type of wireless transmission is referred to as "near-field." Various modulation schemes used in typical RF communications (e.g., amplitude modulation, phase modulation, and frequency modulation) can also be used in near-field magnetic induction communication system.

As used herein, the term "near-field electromagnetic induction (NFeMI) radio communication interface" can refer to a communication interface that can operate near a human body by means of a combination of a magnetic field and electric field without the use of transversal radiating waves. Such NFEMI systems improve a wearable device's signal link budget and extend their range to a complete human body. Whereas RF wireless communication may be accomplished by propagating an RF plane wave through free space, NFEMI communication utilizes non-propagating quasi-static fields.

As used herein, the term "Near-field communication (NFC)" can refer to a set of communication protocols and data exchange formats that enable two or more electronic devices (e.g., a medical device such as an insulin pump and a portable device such as a smartphone) to establish communication with each other by bringing them within a short separation range of each other (e.g., 2 meters or less). NFC allows one- and two-way communication between endpoints, suitable for many applications. NFC uses electromagnetic induction between two loop antennas (located within each other's near-field) to effectively form an air-core transformer that allows them to exchange information. The NFC interface operates based on similar principles as the NFMI interface 322 and uses the same high-frequency (HF) band. However, NFMI extends the range of NFC (e.g., from a distance of 1-4 inches for NFC, to up to 9 feet for NFMI). At around 13 MHz, NFMI provides a data rate of over 400 Kbps per frequency channel, up to 10 separate frequency channels and 10 sub-channels per frequency channel using time division (e.g., a hundred separate wireless links inside a single WBAN). In one non-limiting implementation, NFC-enabled devices that are described herein can exchange information in accordance with any NFC standards that cover communications protocols and data exchange formats. NFC standards cover communications protocols and data exchange formats and are based on existing radio-frequency identification (RFID) standards including ISO/IEC 14443. The standards include ISO/IEC 18092 and those defined by the NFC Forum. In addition to the NFC Forum, the GSM Association (GSMA) group defined a platform for the deployment of GSMA NFC Standards within mobile handsets.

RFID systems can operate in low frequency (LF), high frequency (HF), and ultra-high frequency (UHF) bands, and thus can be categorized by the frequency band within which they operate: low frequency, high frequency, and ultra-high frequency. In addition, there are also two broad categories of systems—passive and active RFID. The LF band covers frequencies from 30 KHz to 300 KHz (e.g., some LF RFID systems operate at 125 KHz, while others operate at 134 KHz). The RFID HF communication interface 326 can operate in a HF band that ranges from 3 to 30 MHz, with communications ranges between 10 cm and 1 m. There are several HF RFID standards, such as the ISO 15693 standard for tracking items, and the ECMA-340 and ISO/IEC 18092 standards for Near Field Communication (NFC), the ISO/IEC 14443 A and ISO/IEC 14443 standards. The UHF frequency band covers the range from 300 MHz to 3 GHz, and the range of some UHF systems can be as long as 12 m with faster data transfer rates than LF or HF. The UHF frequency band is regulated by a single global standard called the ECPglobal Gen2 (ISO 18000-63) UHF standard.

The low power wide area network (LPWAN) communication interfaces can include interfaces such as a Long Term Evolution for Machines (LTE-M) communication interface (LTE-Cat M1) and/or a narrowband-IoT (NB-IoT) communication interface (not illustrated). NB-IOT and LTE-M are two newer low power wide area (LPWA) technologies that were developed for IOT applications. Both are protocols for low bandwidth cellular communications that connect to the internet devices that need to transmit small amounts of data, with the lower costs (both hardware and subscription) and the higher battery life.

The various communication interfaces mentioned above are non-limiting, and can be implemented in accordance with any known standards including those mentioned above. However, it should be appreciated that the number of communication interfaces that are included as part of the communication module 310 can vary depending on the implementation.

A controller (not illustrated) can be configured to control which ones of the communication interfaces are selected and used by a device or component of the wireless body area network to communicate data with other devices or components that are part of the wireless body area network. For example, the controller is configured to select which one of the communication interfaces is to be used at any particular time and switch between which one of the communication interfaces is enabled and used by a device or component of the wireless body area network to communicate data with other devices or components that are part of the wireless body area network.

Referring again to FIG. 3, the display element 311 is suitably configured to enable the device 300 to render and display various screens, insight messages, notifications, GUIs, GUI control elements, drop down menus, auto-fill fields, text entry fields, message fields, or the like. Of course, the display element 311 may also be utilized for the display of other information during the operation of the device 300, as is well understood. Notably, the specific configuration, operating characteristics, size, resolution, and functionality of the display element 310 can vary depending upon the practical implementation of the device 300. For example, if the device 300 is a laptop computer, then the display element 311 may be a relatively large monitor. Alternatively, if the device 300 is a cellular telephone device (e.g., smartphone), then the display element 311 may be a relatively small integrated display screen, such as a touch-sensitive screen.

Figure 4:
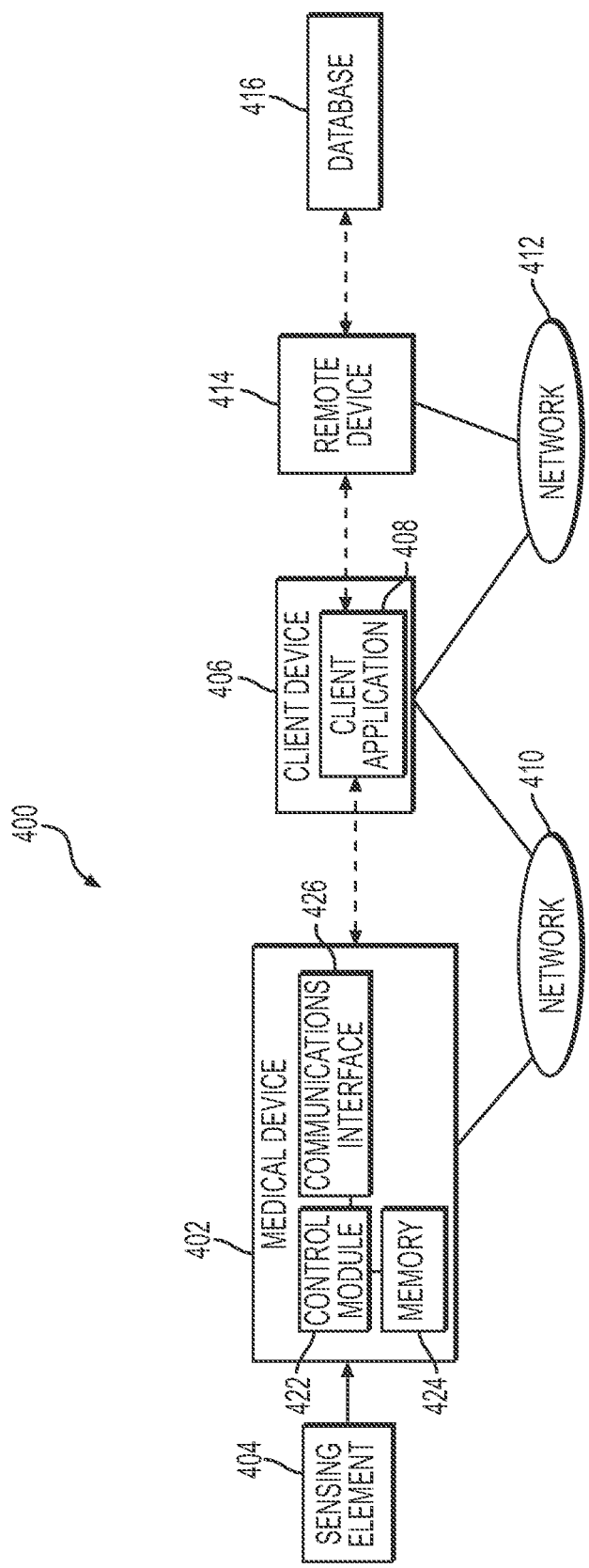
FIG. 4 is a block diagram of an exemplary patient monitoring system.

FIG. 4 depicts an exemplary embodiment of a patient monitoring system 400. The patient monitoring system 400 includes a medical device 402 that is communicatively coupled to a sensing element 404 that is inserted into the body of a patient or otherwise worn by the patient to obtain measurement data indicative of a physiological condition in the body of the patient, such as a sensed glucose level. The medical device 402 is communicatively coupled to a client device 406 via a communications network 410, with the client device 406 being communicatively coupled to a remote device 414 via another communications network 412. In this regard, the client device 406 may be non-medical device that functions as an intermediary for uploading or otherwise providing measurement data from the medical device 402 to the remote device 414. It should be appreciated that FIG. 4 depicts a simplified representation of a patient monitoring system 400 for purposes of explanation and is not intended to limit the subject matter described herein in any way.

In exemplary embodiments, the client device 406 is realized as a mobile phone, a smartphone, a tablet computer, or other similar mobile electronic device; however, in other embodiments, the client device 406 may be realized as any sort of electronic device capable of communicating with the medical device 402 via network 410, such as a laptop or notebook computer, a desktop computer, or the like. In exemplary embodiments, the network 410 is realized as a Bluetooth network, a ZigBee network, or another suitable personal area network. That said, in other embodiments, the network 410 could be realized as a wireless ad hoc network, a wireless local area network (WLAN), or local area network (LAN). The client device 406 includes or is coupled to a display device, such as a monitor, screen, or another conventional electronic display, capable of graphically presenting data and/or information pertaining to the physiological condition of the patient. The client device 406 also includes or is otherwise associated with a user input device, such as a keyboard, a mouse, a touchscreen, or the like, capable of receiving input data and/or other information from the user of the client device 406.

In exemplary embodiments, a user, such as the patient, the patient's doctor or another healthcare provider, or the like, manipulates the client device 406 to execute a client application 408 that supports communicating with the medical device 402 via the network 410. In this regard, the client application 408 supports establishing a communications session with the medical device 402 on the network 410 and receiving data and/or information from the medical device 402 via the communications session. The medical device 402 may similarly execute or otherwise implement a corresponding application or process that supports establishing the communications session with the client application 408. The client application 408 generally represents a software module or another feature that is generated or otherwise implemented by the client device 406 to support the processes described herein. Accordingly, the client device 406 generally includes a processing system and a data storage element (or memory) capable of storing programming instructions for execution by the processing system, that, when read and executed, cause processing system to create, generate, or otherwise facilitate the client application 408 and perform or otherwise support the processes, tasks, operations, and/or functions described herein. Depending on the embodiment, the processing system may be implemented using any suitable processing system and/or device, such as, for example, one or more processor devices, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 406 and the medical device 402 establish an association (or pairing) with one another over the network 410 to support subsequently establishing a point-to-point or peer-to-peer communications session between the medical device 402 and the client device 406 via the network 410. For example, in accordance with one embodiment, the network 410 is realized as a Bluetooth network, wherein the medical device 402 and the client device 406 are paired with one another (e.g., by obtaining and storing network identification information for one another) by performing a discovery procedure or another suitable pairing procedure. The pairing information obtained during the discovery procedure allows either of the medical device 402 or the client device 406 to initiate the establishment of a secure communications session via the network 410.

In one or more exemplary embodiments, the client application 408 is also configured to store or otherwise maintain an address and/or other identification information for the remote device 414 on the second network 412. In this regard, the second network 412 may be physically and/or logically distinct from the network 410, such as, for example, the Internet, a cellular network, a wide area network (WAN), or the like. The remote device 414 generally represents a server or other computing device configured to receive and analyze or otherwise monitor measurement data, event log data, and potentially other information obtained for the patient associated with the medical device 402. In exemplary embodiments, the remote device 414 is coupled to a database 416 configured to store or otherwise maintain data associated with individual patients. In practice, the remote device 414 may reside at a location that is physically distinct and/or separate from the medical device 402 and the client device 406, such as, for example, at a facility that is owned and/or operated by or otherwise affiliated with a manufacturer of the medical device 402. For purposes of explanation, but without limitation, the remote device 414 may alternatively be referred to herein as a server.

Still referring to FIG. 4, the sensing element 404 generally represents the component of the patient monitoring system 400 that is configured to generate, produce, or otherwise output one or more electrical signals indicative of a physiological condition that is sensed, measured, or otherwise quantified by the sensing element 404. In this regard, the physiological condition of a patient influences a characteristic of the electrical signal output by the sensing element 404, such that the characteristic of the output signal corresponds to or is otherwise correlative to the physiological condition that the sensing element 404 is sensitive to. In exemplary embodiments, the sensing element 404 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 404.

The medical device 402 generally represents the component of the patient monitoring system 400 that is communicatively coupled to the output of the sensing element 404 to receive or otherwise obtain the measurement data samples from the sensing element 404 (e.g., the measured glucose and characteristic impedance values), store or otherwise maintain the measurement data samples, and upload or otherwise transmit the measurement data to the remote device 414 or server via the client device 406. In one or more embodiments, the medical device 402 is realized as an infusion device 102, 200 configured to deliver a fluid, such as insulin, to the body of the patient. That said, in other embodiments, the medical device 402 could be a standalone sensing or monitoring device separate and independent from an infusion device (e.g., sensing arrangement 104, 504). It should be noted that although FIG. 4 depicts the medical device 402 and the sensing element 404 as separate components, in practice, the medical device 402 and the sensing element 404 may be integrated or otherwise combined to provide a unitary device that can be worn by the patient.

In exemplary embodiments, the medical device 402 includes a processor 422, a data storage element 424 (or memory), and a communications interface 426. The processor 422 generally represents the hardware, circuitry, logic, firmware and/or other component(s) of the medical device 402 that is coupled to the sensing element 404 to receive the electrical signals output by the sensing element 404 and perform or otherwise support various additional tasks, operations, functions and/or processes described herein. Depending on the embodiment, the processor 422 may be implemented or realized with a general purpose processor device, a microprocessor device, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the processor 422 includes an analog-to-digital converter (ADC) or another similar sampling arrangement that samples or otherwise converts an output electrical signal received from the sensing element 404 into corresponding digital measurement data value. In other embodiments, the sensing element 404 may incorporate an ADC and output a digital measurement value.

The communications interface 426 generally represents the hardware, circuitry, logic, firmware and/or other components of the medical device 402 that are coupled to the processor 422 for outputting data and/or information from/to the medical device 402 to/from the client device 406. For example, the communications interface 426 may include or otherwise be coupled to one or more transceiver modules capable of supporting wireless communications between the medical device 402 and the client device 406. In exemplary embodiments, the communications interface 426 is realized as a Bluetooth transceiver or adapter configured to support Bluetooth Low Energy (BLE) communications.

In exemplary embodiments, the remote device 414 receives, from the client device 406, measurement data values associated with a particular patient (e.g., sensor glucose measurements, acceleration measurements, and the like) that were obtained using the sensing element 404, and the remote device 414 stores or otherwise maintains the historical measurement data in the database 416 in association with the patient (e.g., using one or more unique patient identifiers). Additionally, the remote device 414 may also receive, from or via the client device 406, meal data or other event log data that may be input or otherwise provided by the patient (e.g., via client application 408) and store or otherwise maintain historical meal data and other historical event or activity data associated with the patient in the database 416. In this regard, the meal data include, for example, a time or timestamp associated with a particular meal event, a meal type or other information indicative of the content or nutritional characteristics of the meal, and an indication of the size associated with the meal. In exemplary embodiments, the remote device 414 also receives historical fluid delivery data corresponding to basal or bolus dosages of fluid delivered to the patient by an infusion device 102, 200. For example, the client application 408 may communicate with an infusion device 102, 200 to obtain insulin delivery dosage amounts and corresponding timestamps from the infusion device 102, 200, and then upload the insulin delivery data to the remote device 414 for storage in association with the particular patient. The remote device 414 may also receive geolocation data and potentially other contextual data associated with a device 402, 406 from the client device 406 and/or client application 408, and store or otherwise maintain the historical operational context data in association with the particular patient. In this regard, one or more of the devices 402, 406 may include a global positioning system (GPS) receiver or similar modules, components or circuitry capable of outputting or otherwise providing data characterizing the geographic location of the respective device 402, 406 in real-time.

The historical patient data may be analyzed by one or more of the remote device 414, the client device 406, and/or the medical device 402 to alter or adjust operation of an infusion device 102, 200 to influence fluid delivery in a personalized manner. For example, the patient's historical meal data and corresponding measurement data or other contextual data may be analyzed to predict a future time when the next meal is likely to be consumed by the patient, the likelihood of a future meal event within a specific time period, the likely size or amount of carbohydrates associated with a future meal, the likely type or nutritional content of the future meal, and/or the like. Moreover, the patient's historical measurement data for postprandial periods following historical meal events may be analyzed to model or otherwise characterize the patient's glycemic response to the predicted size and type of meal for the current context (e.g., time of day, day of week, geolocation, etc.). One or more aspects of the infusion device 102, 200 that control or regulate insulin delivery may then be modified or adjusted to proactively account for the patient's likely meal activity and glycemic response.

In one or more exemplary embodiments, the remote device 414 utilizes machine learning to determine which combination of historical sensor glucose measurement data, historical delivery data, historical auxiliary measurement data (e.g., historical acceleration measurement data, historical heart rate measurement data, and/or the like), historical event log data, historical geolocation data, and other historical or contextual data are correlated to or predictive of the occurrence of a particular event, activity, or metric for a particular patient, and then determines a corresponding equation, function, or model for calculating the value of the parameter of interest based on that set of input variables. Thus, the model is capable of characterizing or mapping a particular combination of one or more of the current (or recent) sensor glucose measurement data, auxiliary measurement data, delivery data, geographic location, patient behavior or activities, and the like to a value representative of the current probability or likelihood of a particular event or activity or a current value for a parameter of interest. It should be noted that since each patient's physiological response may vary from the rest of the population, the subset of input variables that are predictive of or correlative for a particular patient may vary from other patients. Additionally, the relative weightings applied to the respective variables of that predictive subset may also vary from other patients who may have common predictive subsets, based on differing correlations between a particular input variable and the historical data for that particular patient. It should be noted that any number of different machine learning techniques may be utilized by the remote device 414 to determine what input variables are predictive for a current patient of interest, such as, for example, artificial neural networks, genetic programming, support vector machines, Bayesian networks, probabilistic machine learning models, or other Bayesian techniques, fuzzy logic, heuristically derived combinations, or the like.

The insulin infusion device may incorporate or leverage the control algorithms, processing schemes, and operating methodologies (or suitably modified, updated, or customized versions thereof) of the type described in U.S. Pat. No. 9,526,834 and International (PCT) patent publication number WO 2014/035570; the content of these published documents is incorporated herein by reference.

Figure 5:
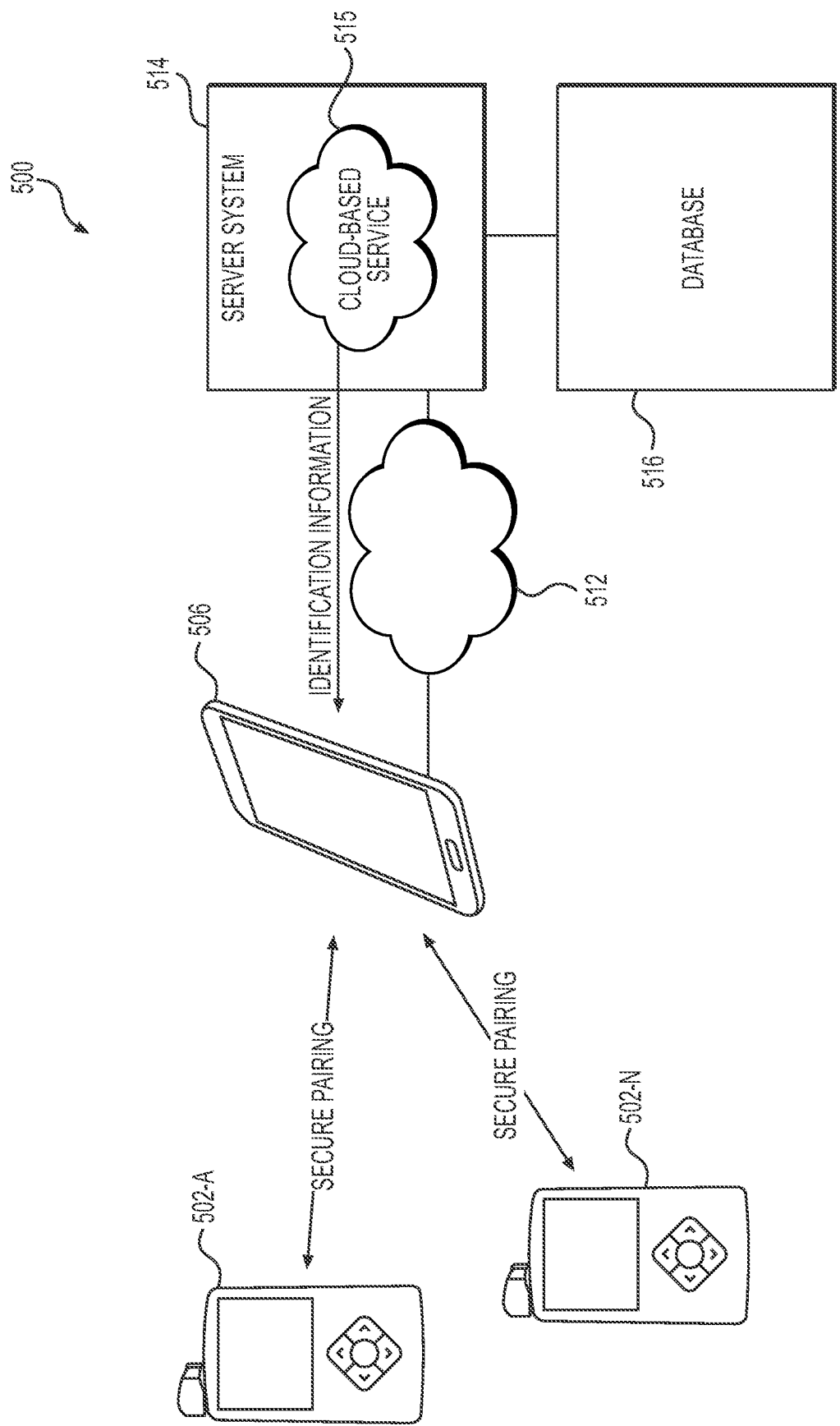
FIG. 5 is a block diagram of a system in accordance with the disclosed embodiments.

FIG. 5 is a block diagram of a medical device system 500 in accordance with the disclosed embodiments. In this non-limiting example, the system 500 includes one or more medical device(s) 502, a non-medical device 506, and a cloud-based computing or server system 514 that hosts a cloud-based service 515.

Each medical device 502 can be a device that is issued or prescribed to a patient by a physician or other health care provider for therapy of a medical condition. Each medical device 502 can be body-worn, implanted, or used episodically. Each medical device 502 can be a long-lived (durable) device, or a device that is used for a short period of time and replaced (disposable). Examples of medical devices include glucose sensors (e.g., continuous glucose monitors), insulin infusion devices (e.g., tubed insulin pumps, or patch insulin pumps), etc. (e.g., the fluid infusion device (or infusion pump) 102 and the sensing arrangement 104 of FIG. 1; the insulin infusion device 202, the glucose sensor 204, and the blood glucose meter 207 of FIG. 2; and the medical device 402 and the sensing element 404 of FIG. 4), The non-medical device 506 can be a device used by a patient to interact with a medical device via a wireless network (not illustrated), such as a smartphone, a smart watch, a tablet, a personal computer, or other general-purpose computing device (e.g., the computer 106 and the command control device (CCD) 109 of FIG. 1; the mobile device 206 and the data uploader 209 of FIG. 2; and the client device 406 of FIG. 4). In one embodiment, the medical device(s) 502 and the non-medical device 506 can communicate with each other over a wireless network using any of the technologies described above. The wireless network can employ one or more of radio frequency (RF), light, ultrasonic, or other emissions to convey information without the use of interconnecting wires. One non-limiting example of a wireless network is a Bluetooth Low Energy (BLE®) body area network (BAN).

The medical devices 502 that will be provided to a particular patient, as well as identification information that identifies each medical device 502, is known prior to delivery to the patient. In accordance with the disclosed embodiments, the cloud-based service 515 hosted by the server system 514 can provide the non-medical device 506 with identification information, which will be referred to below as "first identification information" (e.g., pairing information) for each of the one or more medical device(s) 502 prior to the medical device(s) 502 being deployed or being used (e.g., prior to delivery to the patient or prior to the medical device 502 going on-line). For example, in one scenario, prior to shipping or delivering a medical device 502 to a patient, the cloud-based service 515 can provide first identification information for each medical device (e.g., a serial number and possibly other information such as encryption keys for each medical device) to the non-medical device 506 of the particular patient so that it is known a priori. For example, in one embodiment, when the non-medical device 506 downloads or runs an application for use with the cloud service 515, the cloud-based service can securely provide the non-medical device 506 with identifying or pairing information (e.g., identifiers for the medical device 502 and/or keying information). In some implementations, prior to providing the identifying or pairing information (e.g., identifiers for the medical device 502 and/or keying information), other proof of identity may be required (e.g., a user login) before the cloud-based service can securely provide the non-medical device 506 with identifying or pairing information (e.g., identifiers for the medical device 502 and/or keying information). This first identification information can then be used to establish a secure communication link (e.g., pair) between the devices.

In one embodiment, an implementation of which will described below with reference to FIG. 7, for example, when the medical device 502 is prepared for use (e.g., activated, goes online or is otherwise brought into use by the user), it can broadcast/emit its identification information such that the non-medical device 506 can automatically identify that medical device 502 without having to undergo a conventional association process. Conversely, in another embodiment, an implementation of which will described below with reference to FIG. 8, for example, when the non-medical device 506 is prepared for use (e.g., activated, goes online or is otherwise brought into use by the user), it can broadcast/emit its identification information such that the medical device 502 can automatically identify that non-medical device 506 without having to undergo a conventional association process.

Based on the first identification information, the non-medical device 506 can automatically recognize the medical device 502 without having to initiate a scanning process and, in some implementations, without having to be manually configured with the first identification information. In this way the patient does not have to perform any manual configuration to allow the two devices to pair, such as, entering a serial number of the medical device 502 at the non-medical device 506, or vice versa (e.g., the patient does not have to input any configuration information manually to pair their medical device 502 with their personal non-medical device(s), and vice-versa). This allows secure a radio communication link to be established between a medical device 502 and a non-medical device 506 without any manual intervention by the patient (e.g., after the medical device 502 is delivered to the patient). This way the non-medical device 506 will only pair with medical devices that it is intended to pair with, and the medical device 502 only pairs with non-medical device(s) that it intends to pair with.

Figure 6:
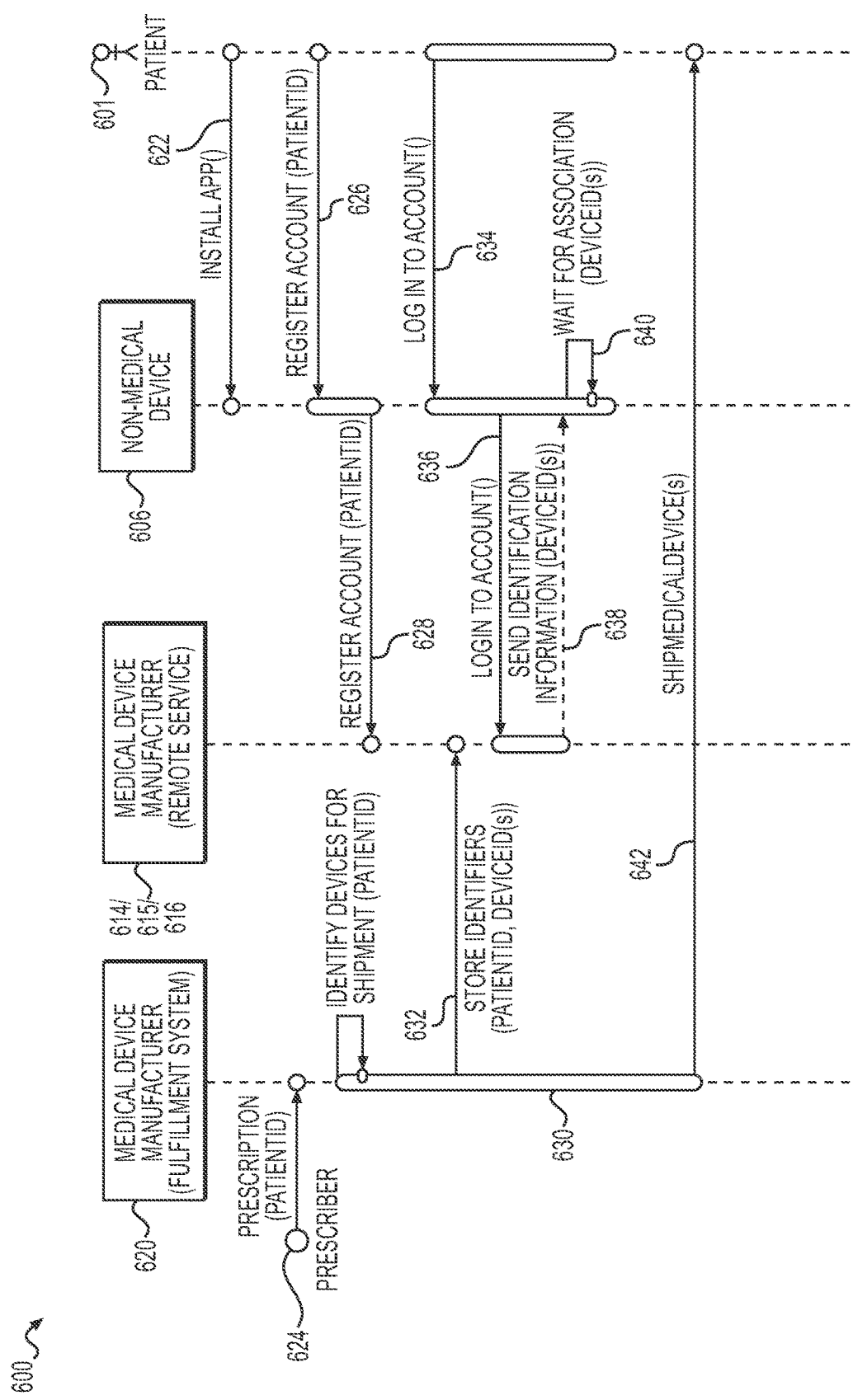
FIG. 6 is a flow diagram that illustrates a method of pre-populating a non-medical device with first identification information for one or more medical devices that will be provided to a patient in accordance with the disclosed embodiments.

FIG. 6 is a flow diagram 600 that illustrates a method of pre-populating a non-medical device 606 with identification information, that will be referred to below as "first identification information," for one or more medical devices that will be provided to a patient 601 in accordance with the disclosed embodiments. FIG. 6 shows the interactions that take place involving a prescriber of medical device(s) 602/604 (e.g., doctor or other health care provider), a manufacturer of a medical device including a fulfillment system 620 and a cloud-based service 615, and a non-medical device 606 of a patient 601.

At 622, the prescriber issues a prescription to the particular patient 601 for the medical device 602/604. For example, a patient is prescribed a medical device 602/604 for treatment of a medical condition. The patient may be prescribed more than one device at one time. This permits one device to be used while the other is undergoing maintenance, such as battery charging. This also may occur if the devices are disposable; several devices may be needed to support an extended period of therapy without a new prescription or refill. An order for the medical device(s) 602/604 can be submitted to the medical device manufacturer. This order may be submitted by the prescribing physician, by the patient (with proof of prescription), or by an authorized third party. The order may alternatively be submitted to a third-party fulfillment provider.

At 624, the patient 601 configures one or more non-medical devices 606 to interact with the medical device(s) 602/604. This interaction may serve the purpose of therapy monitoring, remote control, or the uploading of data to a remote service for analysis and review. The configuration process may involve the installation of software, such as a mobile app. In this case, the patient installs or activates an application (e.g., a mobile application) on their personal non-medical device 606. At 626 and 628, as part of the configuration process, the patient 601 logs in to a user account provided by a cloud-based service operated by the device manufacturer. The patient may be provided with login credentials automatically when the device is ordered. In some cases, the patient 601 may need to register for the service at the time of first login, using some authorizing information provided when the prescription is issued. In this case, the patient 601 registers an account with the cloud service (e.g., CARELINK®) using their personal non-medical device 606.

At 630, the fulfillment system 620 identifies the medical devices (not shown in FIG. 6) that are to be shipped to the patient 601 and retrieves the identification information for those particular medical devices (not shown in FIG. 6). For example, the manufacturer of the medical device 602/604 can uniquely identify each of the particular instances of the medical device(s) 602/604 to be shipped to the patient with its own first identification information that can be used by a non-medical device to distinguish each of the medical device(s) 602/604 from one another. These may be distinguished by serial number or by some other means. Retrieval of the identification information can be performed using any known storage, networking and communication technology including any storage, networking or communication technologies described above.

At 632, the fulfillment system 620 stores the identification information for those particular medical devices (not shown in FIG. 6) in a database of the cloud-based service, and then sends it to the account of the patient 601 (that was created at the cloud service at steps 626 and 628). In one embodiment, the medical device 602/604 manufacturer uploads a unique identification information set for each medical device 602/604 to the patient's user account at the remote, cloud-based service. This data set can include any or all of: a device serial number (also stored in the device); another numeric identifier (also stored in the device); a cryptographic public signature verification key, with a corresponding unique private signing key having previously been stored in the medical device 602/604; a cryptographic private payload decryption key, with a corresponding unique public encryption key having previously been stored in the medical device 602/604; and/or one or more cryptographic certificates, each containing one or more public or private keys and associated metadata, where keys may be used for signing/signature verification, payload encryption/decryption, or both, etc. Information related to this data set, such as cryptographic keys, may be stored in the database.

At 634 and 636, the patient 601 then logs into or otherwise accesses their account using their non-medical device 606, and at 638, the cloud-based service 615 retrieves the first identification information for each of the medical devices (not shown in FIG. 6) that will be sent to the patient 601, and communicates the first identification information (e.g., codes) for each of the identified medical devices (not shown in FIG. 6) to the non-medical device 606 of the patient 601.

At this point the non-medical device 606 has been pre-populated with the first identification information for each of the medical devices (not shown in FIG. 6) that will be shipped to the patient 601 (or that have been shipped to the patient 601 at a prior time). At 640, the non-medical device 606 waits for an association message (e.g., association request or association announcement) from one of the medical devices (not shown in FIG. 6). At 642, the medical devices (not shown in FIG. 6) can then be then shipped to the patient 601. In the event that the devices fail to arrive (e.g., within a threshold period of time or other measure), the cloud-based service may signal the patient's non-medical device 606 to delete the identification information of the lost devices. The cloud-based service may also configure the identification information to expire automatically if it is not used within a certain period of time.

Although not shown, the methodologies described above may be extended such that the cloud-based service provides the patient's non-medical device 606 with wireless traffic encryption keys in addition to keying material used for identification and authentication. In one embodiment, the wireless traffic encryption keys and keying material can be communicated to the patient's non-medical device 606 along with the identification information for each medical device. In another embodiment, the wireless traffic encryption keys and keying material can be communicated to the patient's non-medical device 606 separately from the identification information for each medical device (e.g., the identification information, wireless traffic encryption keys and keying material can be communicated in separate transmissions). The methodologies described above may be extended to include a more robust authentication technique, such as a cryptographic challenge-response handshake, that must be completed between the medical device 602/604 and non-medical device 606 before a connection is established. This extension provides additional security.

Figure 7:
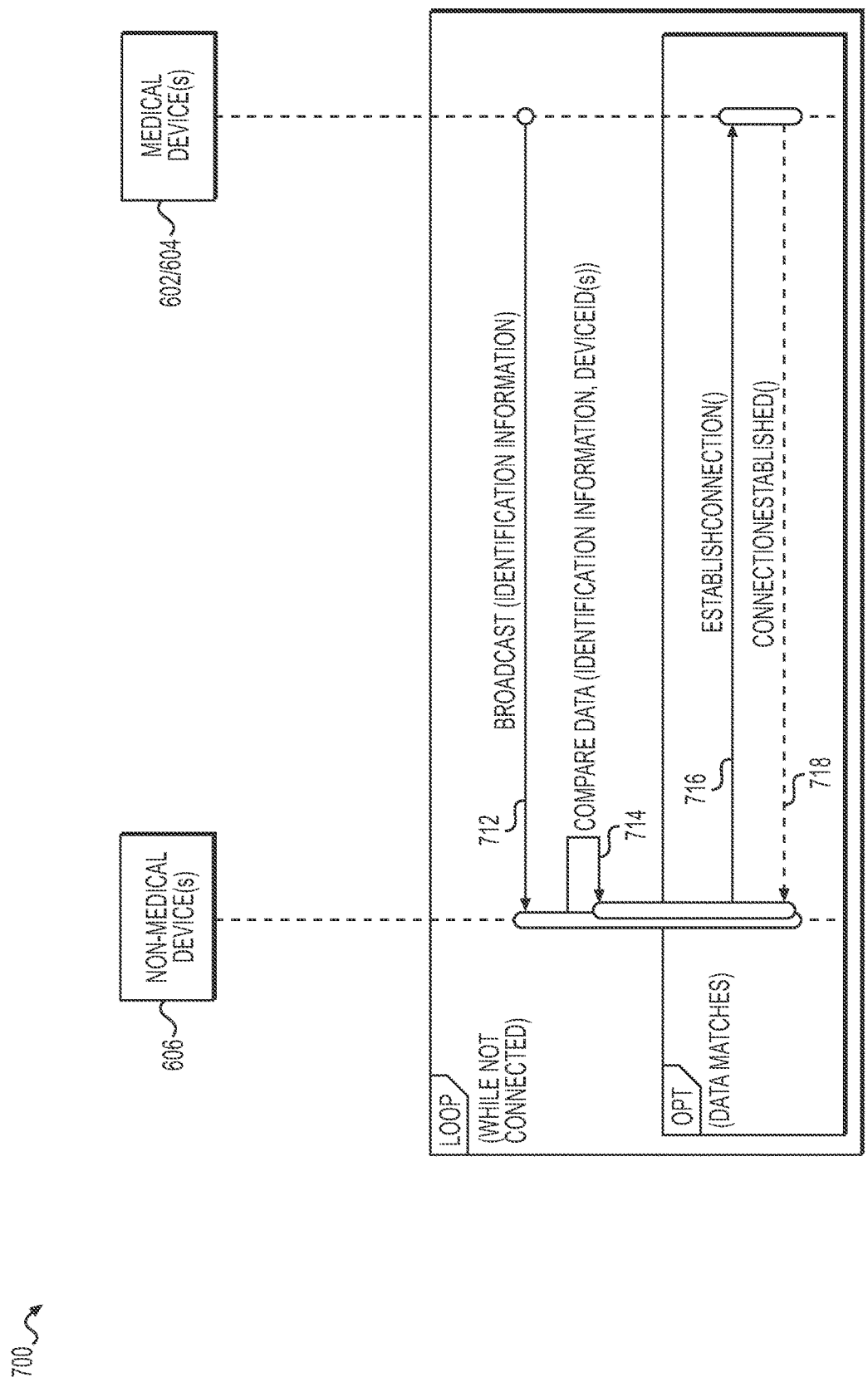
FIG. 7 is a flow diagram that illustrates a method for associating a non-medical device with one more medical devices in accordance with the disclosed embodiments.

FIG. 7 is a flow diagram that illustrates a method 700 for associating a non-medical device 606 with one more medical devices 602/604 in accordance with the disclosed embodiments. FIG. 7 shows interactions that can occur during an association process in accordance with the disclosed embodiments. The actions can occur, for example, whenever a patient activates one of their medical devices 602/604 or puts it into service. FIG. 7 describes one non-limiting implementation of actions that can take place after step 638 of FIG. 6, where the identifiers are sent from the cloud service to the non-medical device 606 of the patient, and step 640 of FIG. 6, when the non-medical device 606 is awaiting an association message from one of the medical devices 602/604.

At step 712, the particular medical device 602/604 will begin transmitting a request to associate along with its identification information, which will be referred to below as "second identification information" to differentiate it from the "first identification information" referred to above with reference to FIG. 6. The patient receives and begins using the medical device 602/604. Each medical device 602/604 can wirelessly broadcast respective second identification information. Each broadcast can include any or all of: a device serial number or other numeric identifier of the broadcasting device; a deterministic function (such as a hash) of a device serial number of the broadcasting device or other numeric identifier of the broadcasting device; a random number, timestamp, or other non-recurring value; any or all of the above, along with a cryptographic signature; any or all of the above, encrypted with a cryptographic key; any or all of the above, encrypted with a cryptographic key and accompanied by a cryptographic signature, etc. Each broadcast may include identical information, or information that varies with each new message transmitted. In some embodiments, the broadcasts can include sending first identification information at first time and second identification information, different from the first identification information, at a second time, after the first time. In some embodiments, the second identification information may be random. For example, the use of time-varying broadcasts and cryptographic signatures helps reduce the risk of a patient's device associating with the wrong device. This also protects against a malicious actor trying to force a patient's non-medical device 606 to associate with another device instead of the medical device 602/604. An attacker not possessing advance knowledge of the secret keys within the medical device 602/604 cannot generate false messages that would be accepted by the patient's device. (An attacker could retransmit valid messages received via eavesdropping at a later time; the use of timestamps referenced to a shared time reference, such as an absolute clock, protects against this).

At step 714, the non-medical device 606 can receive the request and the second identification information and determine whether the second identification information for the medical device 602/604 is that of a medical device that the non-medical device 606 is to associate with by comparing it to stored first identification information that was provided (in FIG. 6) to the non-medical device 606 by the cloud service. In essence, the non-medical device 606 determines whether the broadcast received from the medical device 602/604 can be verified. In one embodiment, the patient's non-medical device 606 scans for broadcasts from medical devices 602/604. Upon receiving a broadcast, the non-medical device 606 compares contents of the broadcast with the first identification information provided by the cloud-based service (e.g., as described above with reference to FIG. 6). In the case of simple numeric identifiers, this may be a simple equality test. If the identification information includes a signature verification key, the patient's non-medical device 606 uses the key to verify that the signature included in the broadcast is valid. If the identification information includes a data decryption key, the patient's non-medical device 606 uses the key to decrypt the second identification information from the broadcast and inspect other data stored within the encrypted second identification information. In one embodiment, the first identification information can be a hash value of the second identification information (e.g., an identifier of the medical device 602/ 604). In this case, the non-medical device 606 performs a hash operation with respect to the second identification information to compare the resulting hash value to the first identification information, and determine whether the broadcast received from the medical device 602/604 can be verified.

When the non-medical device 606 determines (at step 714) that the second identification information for the medical device 602/604 is not that of a medical device that the non-medical device 606 is to associate with (e.g., the broadcast received cannot be verified), then it is ignored. If a large number of invalid broadcasts is received, the patient's non-medical device 606 may discontinue scanning temporarily to conserve power. It may also warn the patient of possible interference. By contrast, when the non-medical device 606 determines (at step 714) that the second identification information for the medical device 602/604 is that of a medical device that the non-medical device 606 is to associate with (e.g., the broadcast received can be verified), then at step 716, the non-medical device 606 can send a request with appropriate authentication information or first identification information to the medical device 602/604. At step 718, the medical device 602/604 can process the authentication information or the first identification information to confirm that the authentication information or the identification information is valid, and if so, automatically self-authorize to automatically associate with that non-medical device 606 and establish a communication link with that non-medical device 606.

If the second identification information from the received broadcast corresponds to or matches the first identification information previously provided by the cloud-based service to the patient's non-medical device 606, the non-medical device 606 and the medical device 602/604 can automatically establish a network connection in some embodiments. This connection may be a permanent (e.g., paired and bonded) connection, or a temporary (e.g., paired) connection. After the connection is established, the medical device 602/604 may cease transmitting identifying broadcasts. It may also continue transmitting them to allow other patient-owned devices to associate.

Figure 8:
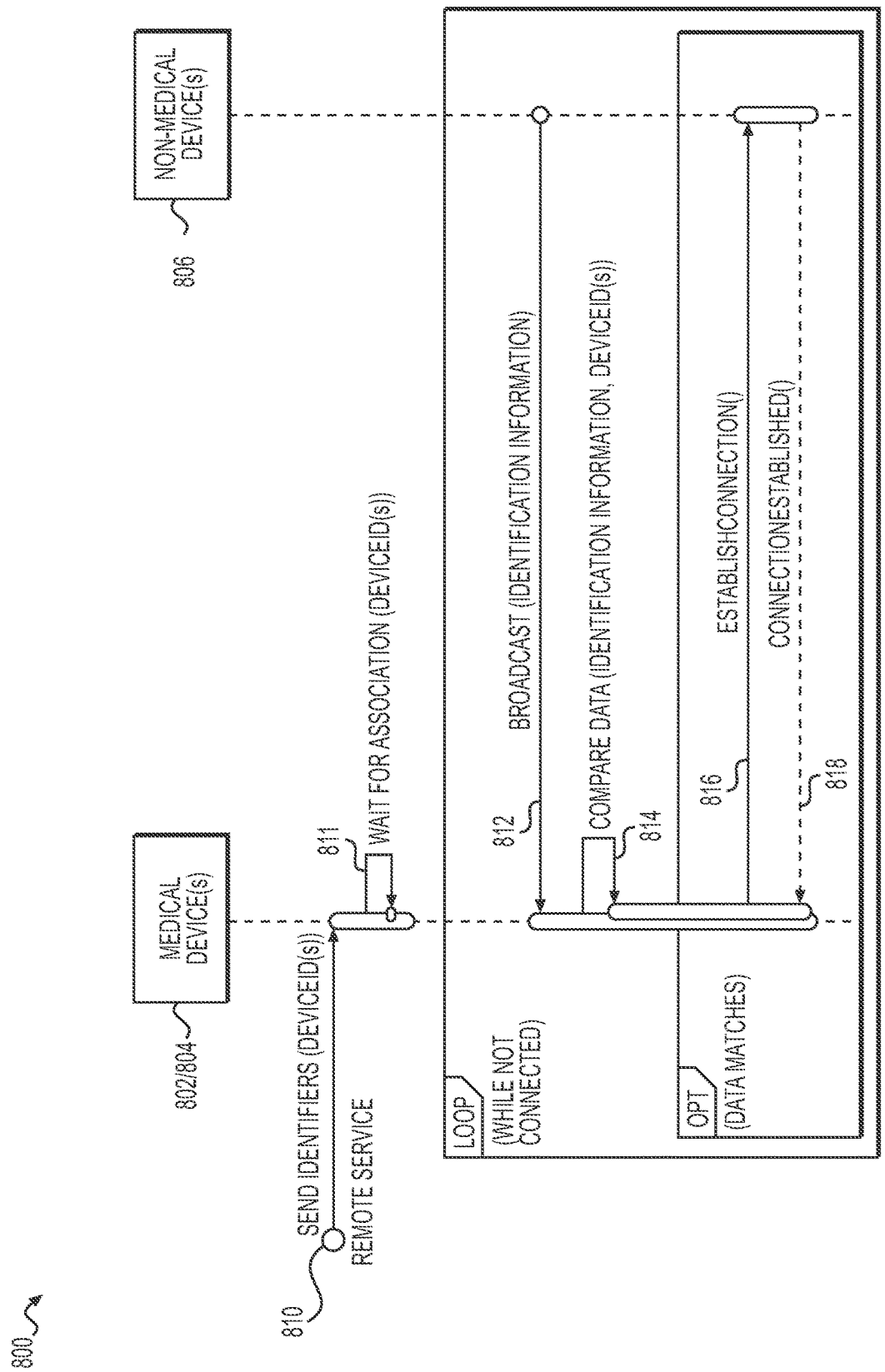
FIG. 8 is a flow diagram that illustrates another method for associating a non-medical device with one more medical devices in accordance with the disclosed embodiments.

FIG. 8 is a flow diagram that illustrates another method 800 for associating a non-medical device 606 with one more medical devices 602/604 in accordance with the disclosed embodiments. As explained above, a fulfillment system can store first identification information for particular non-medical devices 806 of the patient that the patient has pre-authorized to interact with medical devices that will be issued or that have been issued to the patient, as well as first identification information for those particular medical devices. Stated differently, the medical device 802/804 can be pre-populated with the first identification information for each non-medical device 806 that the patient has authorized to be used in conjunction with their medical device 802/804(s). For example, this first identification information can be stored in a database associated with the cloud-based service and the patient's account. In contrast to FIG. 7, in this embodiment, the patient's non-medical device 806 may transmit broadcasts that are to be validated by one or more of the medical device 802/804.

The actions shown in FIG. 8 can occur, for example, when a patient prepares one of their medical devices 802/804 for use (e.g., activates one of their medical devices 802/804 (that was prescribed by a prescriber) or puts it into service (e.g., using a cloud-based service such as CARELINK®)), or alternatively, whenever a patient logs into their account or activates an application (e.g., a mobile application) on their personal non-medical device 806 that is associated with a cloud-based service (such as CARELINK®). FIG. 8 describes one non-limiting implementation of actions that can take place after first identification information (e.g., identifiers) are sent (at 810) from the cloud service to at least one medical device 802/804 of the patient, and when the medical device 802/804 is awaiting an association message (e.g., association request or association announcement) (at 811) from a non-medical device 806 that is authorized by the patient to be used in conjunction with the medical device 802/804.

At step 812, the particular non-medical device 806 can transmit/broadcast a request to associate along with its second identification information. At step 814, the medical device 802/804 can receive the request and second identification information (e.g., when it is within a threshold distance from non-medical device 806) and determine whether the second identification information for the non-medical device 806 is that of a non-medical device that patient has authorized to automatically associate with medical device(s) 802/804 of that patient. This can be done by comparing the second identification information for the non-medical device 806 to stored first identification information that was provided (at 810) to the medical device 802/804 by the cloud-based service. Depending on the scenario, the first identification information and the second identification information can be the same or different. In other words, when the non-medical device and the medical device 802/804 have been authorized to associate with each other, the second identification information from the non-medical device should match an instance of first identification information stored at the medical device 802/804. By contrast, when the non-medical device and the medical device 802/804 have not been authorized to associate with each other, the second identification information from the non-medical device will not match an instance of first identification information stored at the medical device 802/804.

When the medical device 802/804 determines (at step 814) that the second identification information for the non-medical device 806 is that of a non-medical device that the medical device 802/804 is authorized to associate with, then, in one embodiment, at step 816, the medical device 802/804 can send a request with appropriate authentication (or identifying) information to the non-medical device 806. In other embodiments, when the medical device 802/804 determines (at step 814) that the first identification information for the non-medical device 806 is that of a non-medical device that the medical device 802/804 is authorized to associate with, then at step 816, the medical device 802/804 can send a request without authentication information (e.g., the medical device completes the authentication without any further exchange of authentication data). At step 818, the non-medical device 806 can process the authenticating or second identification information to confirm that it is valid, and if so, automatically self-authorize to automatically associate with that medical device 802/804 and establish a communication link with that medical device 802/804.

Figure 9:
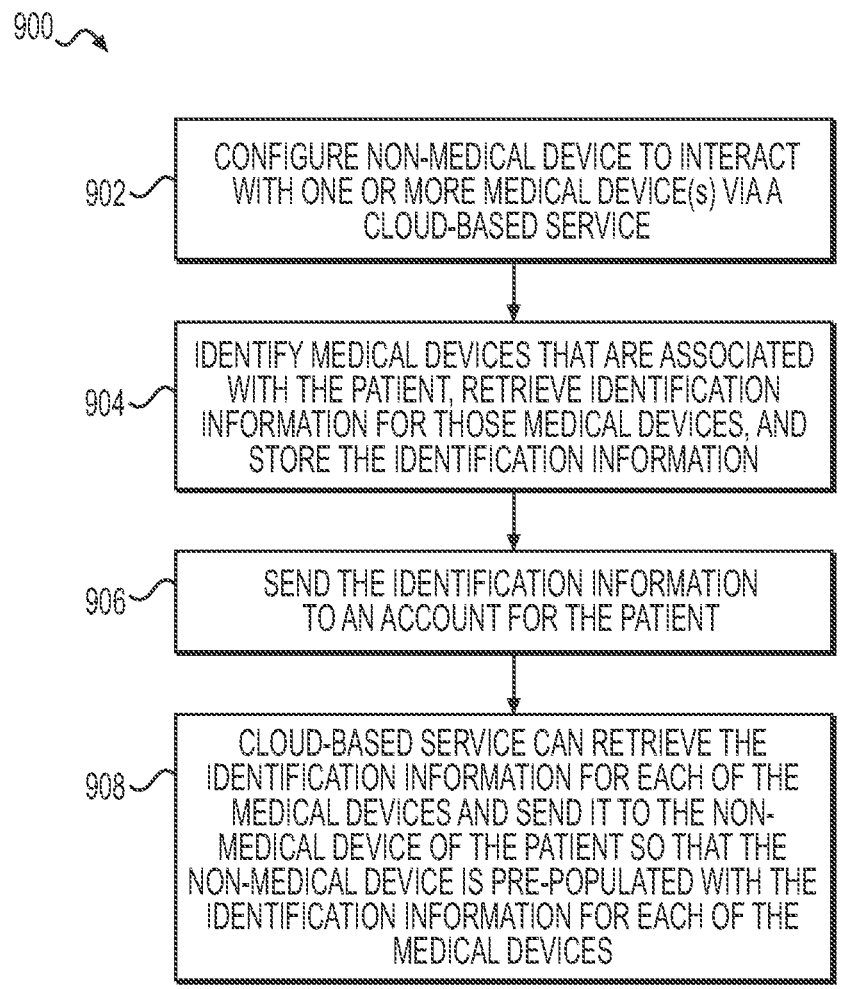
FIG. 9 is a flow chart that illustrates a method of pre-populating a non-medical device with first identification information for one or more medical devices that will be provided to a patient in accordance with the disclosed embodiments.
Figure 10:
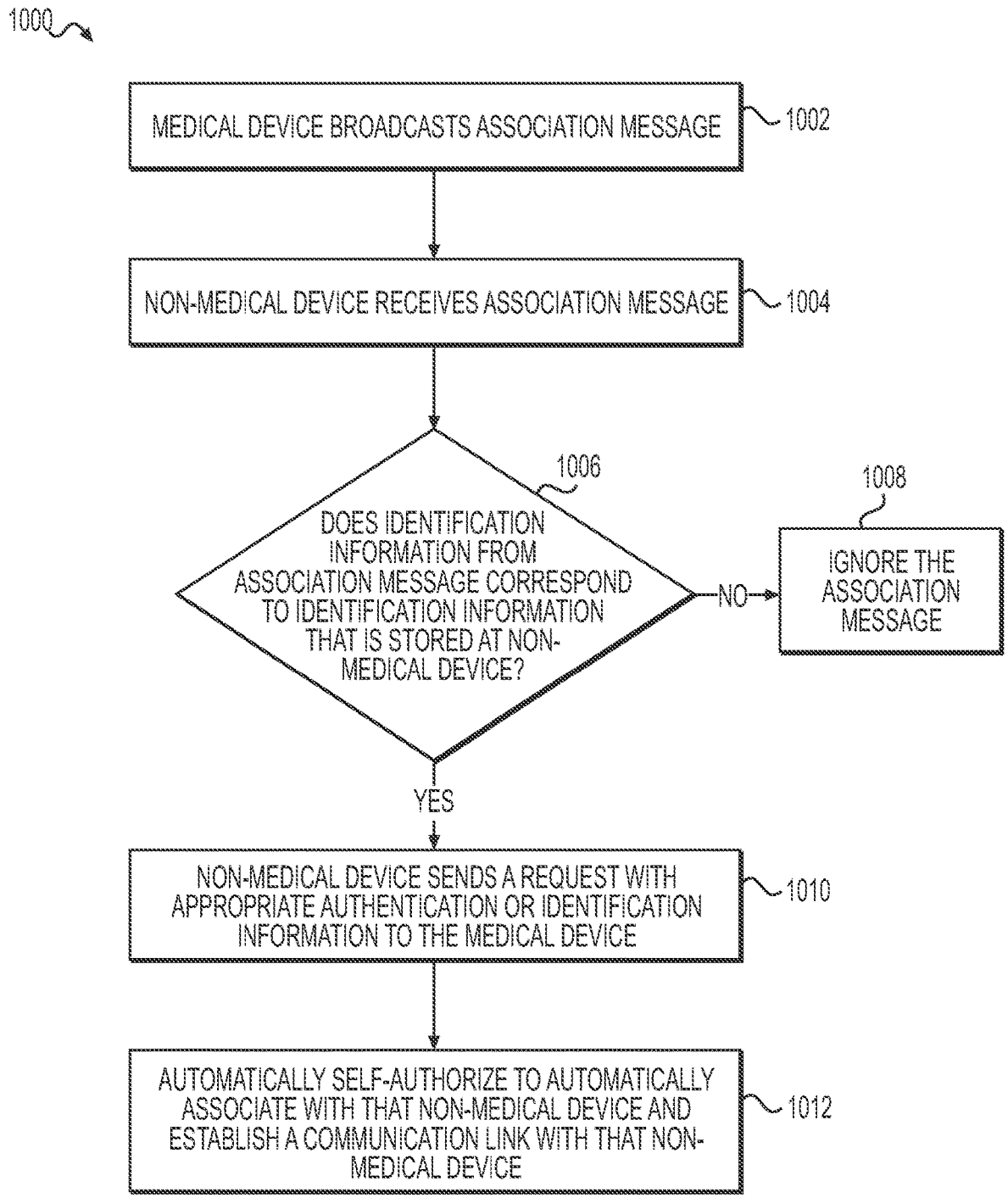
FIG. 10 is a flow chart that illustrates a method for associating a non-medical device with one more medical devices in accordance with the disclosed embodiments.

FIG. 9 is a flow chart that illustrates a method 900 of pre-populating a non-medical device with first identification information for one or more medical devices that will be provided to a patient 601 in accordance with the disclosed embodiments. FIG. 10 is a flow chart that illustrates a method 1000 for associating a non-medical device with one more medical devices in accordance with the disclosed embodiments. As a preliminary matter, it should be understood that the steps of the methods 900, 1000 are not necessarily limiting. With reference to methods 900, 1000, steps can be added, omitted, and/or performed simultaneously without departing from the scope of the appended claims. It should be appreciated that the methods 900, 1000 may include any number of additional or alternative tasks, that the tasks shown in FIGS. 9 and 10 need not be performed in the illustrated order, and that the methods 900, 1000 may be incorporated into a more comprehensive procedure or process having additional functionality not described in detail herein. Moreover, one or more of the tasks shown in FIGS. 9 and 10 could potentially be omitted from an embodiment of the methods 900, 1000 as long as the intended overall functionality remains intact. It should also be understood that the illustrated methods 900, 1000 can be stopped at any time. The methods 900, 1000 are computer-implemented in that various tasks or steps that are performed in connection with the methods 900, 1000 may be performed by software, hardware, firmware, or any combination thereof. For illustrative purposes, the following description of the methods 900, 1000 may refer to elements mentioned above in connection with FIGS. 1-8.

In certain embodiments, some or all steps of this process, and/or substantially equivalent steps, are performed by execution of processor-readable instructions stored or included on a processor-readable medium. For instance, in the description of FIGS. 9 and 10 that follows, the non-medical client device and the medical device will be described as performing various acts, tasks or steps, but it should be appreciated that this refers to processing system(s) of these entities executing instructions to perform those various acts, tasks or steps. Depending on the implementation, the methods 900, 1000 can be performed by an application at the non-medical client device and/or an application at the medical device. Both the medical device and the non-medical client device are capable of confirming whether there is a communication link between them and notifying the user if the communication link is not established or adequate, in which case one or more notifications, warnings, alerts or alarms on the medical device or non-medical device can be activated to alert the user that the communication link between the non-medical client device and the medical device is inadequate. The notifications, warnings, alerts or alarms can be, for example, visual, haptic and/or audio alarms. In some embodiments, the visual, haptic and/or audio alarms can be implemented in specific sequences of visual, audio and haptics for different messages. For example, flashes or vibration followed by a pause can be used to indicate lack of a communication link between the devices. Furthermore, in the description of FIGS. 9 and 10, a particular example is described in which the non-medical client device and/or the medical device perform certain actions by interacting with other elements of the system described above with reference to FIGS. 1-8.

Referring again to FIG. 9, the method 900 of pre-populating a non-medical device with first identification information for one or more medical devices that will be provided to a patient begins at 902, when a patient configures one or more non-medical devices to interact with one or more medical device(s). via an application on their personal non-medical device. As part of the configuration process, the patient may log into or otherwise access a user account provided by a cloud-based service operated by the device manufacturer.

At 904, a fulfillment system 920 can identify medical devices that are associated with the patient, retrieve first identification information for each of those particular medical devices (e.g., a serial number or other identifying information), and store the first identification information for those particular medical devices in a database of the cloud-based service. Depending on the implementation, the first identification information can be a unique identification information set (described above) for each medical device. Information related to this data set, such as cryptographic keys, may be stored in a database. In some embodiments, to provide additional security, the method 900 may be extended such that the cloud-based service provides the patient's non-medical device with wireless traffic encryption keys in addition to keying material used for identification and authentication, and/or to include a more robust authentication technique, such as a cryptographic challenge-response handshake, that must be completed between the medical device and non-medical device before a connection is established.

At 906, the first identification information can be sent to an account for the patient that is maintained by the cloud-based service. When the patient logs into or accesses their account using their non-medical device, at 908, the cloud-based service can retrieve the first identification information for each of the medical devices and send it to the non-medical device of the patient. At this point the non-medical device is pre-populated with the first identification information that is unique for each of the medical devices, and waits for an association message (e.g., association request or association announcement) from one of the medical devices (not shown in FIG. 9).

As shown in FIG. 10, the method 1000 for associating a non-medical device with one more medical devices begins at step 1002, where the particular medical device will begin transmitting/broadcasting a request to associate along with its second identification information that may or may not be the same as an instance of the first identification information stored at the particular non-medical device. Each broadcast can include any or all of: a device serial number or other numeric identifier; a deterministic function (such as a hash) of a device serial number or other numeric identifier; a random number, timestamp, or other non-recurring value; any or all of the above, along with a cryptographic signature; any or all of the above, encrypted with a cryptographic key; any or all of the above, encrypted with a cryptographic key and accompanied by a cryptographic signature, etc. In some embodiments, the first identification information can be a hash value of the second identification information (e.g., identifier of the medical device 602/604). In this case, the non-medical device 606 performs a hash operation with respect to the second identification information to compare the resulting hash value to the first identification information, and determine whether the broadcast received from the medical device 602/604 can be verified. In some embodiments, each broadcast may include identical information, or information that varies with each new message transmitted. The use of time-varying broadcasts and cryptographic signatures helps reduce the risk of a patient's device associating with the wrong device. This also protects against a malicious actor trying to force a patient's non-medical device to associate with another device instead of the medical device. For example, an attacker not possessing advance knowledge of the secret keys within the medical device cannot generate false messages that would be accepted by the patient's device.

The patient's non-medical device scans for broadcasts from medical devices. At step 1004, the non-medical device can receive an association message (e.g., association request or association announcement) that is broadcast by a particular medical device. The association message can include the second identification information for the medical device that transmitted the association message.

At step 1006, the non-medical device can determine whether the second identification information for the medical device is that of a medical device that the non-medical device has been permitted to associate with by comparing it to an instance of the stored first identification information that was provided (in FIG. 9) to the non-medical device by the cloud service. In essence, the non-medical device determines whether the broadcast received from the medical device can be verified as being from medical device that is permitted to communicate with the non-medical device. In one embodiment, upon receiving a broadcast, the non-medical device compares its contents with the identification information that provided by the cloud-based service (at 908 of FIG. 9). In the case of simple numeric identifiers, this may be a simple equality test. If the identification information includes a signature verification key, the patient's non-medical device uses the key to verify that the signature included in the broadcast is valid. If the identification information includes a data decryption key, the patient's non-medical device uses the key to decrypt the broadcast and inspect other data stored within.

When the non-medical device determines (at step 1006) that the second identification information for the medical device is not that of a medical device that the non-medical device is to associate with (e.g., the broadcast received cannot be verified), then at 1008, the association message can be ignored. If a large number of invalid broadcasts are received, the patient's non-medical device may discontinue scanning temporarily to conserve power. It may also warn the patient of possible interference.

By contrast, when the non-medical device determines (at step 1006) that the second identification information for the medical device is that of a medical device that the non-medical device is permitted to associate with (e.g., the broadcast received can be verified as valid), then, in one embodiment, at step 1010, the non-medical device can send a request with appropriate authentication or first identification information to the medical device. In other embodiments, when the medical device determines (at step 1006) that the authentication or first identification information for the non-medical device is that of a non-medical device that the medical device is authorized to associate with, then at step 1010, the medical device 802/804 can send a request without authentication information (e.g., the medical device completes the authentication without any further exchange of authentication data). At step 1012, the medical device can process the authentication or first identification information to confirm that the identification information is valid, and if so, automatically self-authorize to automatically associate with that non-medical device and establish a communication link with that non-medical device. For example, if the broadcast received corresponds to or matches the identification information provided by the cloud-based service to the patient's non-medical device, the non-medical device and the medical device automatically establish a network connection. This connection may be a permanent (paired and bonded) connection, or a temporary (paired) connection. After the connection is established, the medical device may cease transmitting identifying broadcasts. It may also continue transmitting them to allow other patient-owned devices to associate.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A client device comprising:
   one or more transceivers;
   one or more memories; and
   one or more processors, communicatively coupled with the one or more transceivers and the one or more memories, wherein the one or more processors are configured to:
   access a user account provided by a cloud-based service;
   prior to delivery of a medical device to a user associated with the user account, retrieve, via the cloud-based service, first identification information associated with the user account and identifying the medical device, and store the retrieved first identification information in the client device for pairing the medical device and the client device;
   receive, from the medical device, second identification information, wherein the second identification information is transmitted independently from data transmitted from the client device; and
   based on determining that the second identification information corresponds to the first identification information, establish a secure communication link with the medical device.

2. The client device of claim 1, wherein the first identification information uniquely identifies the medical device.

3. The client device of claim 1, wherein the first identification information comprises a device serial number associated with the medical device.

4. The client device of claim 1, wherein the first identification information comprises a numeric identifier associated with the medical device.

5. The client device of claim 1, wherein the first identification information comprises a cryptographic public signature verification key.

6. The client device of claim 1, wherein the first identification information comprises a cryptographic private payload decryption key.

7. The client device of claim 1, wherein the first identification information comprises a hash value of the second identification information.

8. The client device of claim 1, wherein the second identification information comprises a numeric identifier associated with the medical device.

9. The client device of claim 1, wherein the second identification information comprises a random number.

10. The client device of claim 1, wherein the second identification information comprises a timestamp.

11. The client device of claim 1, wherein the second identification information comprises a cryptographic signature.

12. The client device of claim 1, wherein the one or more processors are further configured to:
   establish the secure communication link with the medical device without scanning for the medical device or being manually configured with the first identification information.

13. A processor-implemented method performed by a client device, comprising:
   accessing a user account provided by a cloud-based service;
   prior to delivery of a medical device to a user associated with the user account, retrieving, via the cloud-based service, first identification information associated with the user account and identifying the medical device, and storing the retrieved first identification information in the client device for pairing the medical device and the client device;
   receiving, from the medical device, second identification information, wherein the second identification information is transmitted independently from data transmitted from the client device; and
   based on determining that the second identification information corresponds to the first identification information, establishing a secure communication link with the medical device.

14. The method of claim 13, wherein the first identification information uniquely identifies the medical device.

15. The method of claim 13, wherein the first identification information comprises a numeric identifier associated with the medical device.

16. The method of claim 13, wherein the first identification information comprises a cryptographic public signature verification key.

17. The method of claim 13, wherein the first identification information comprises a cryptographic private payload decryption key.

18. The method of claim 12, wherein the second identification information comprises a random number.

19. One or more non-transitory processor-readable media storing instructions which, when executed by one or more processors, cause performance of:
   accessing a user account provided by a cloud-based service;
   retrieving, via the cloud-based service and prior to delivery of a medical device to a user associated with the user account, first identification information associated with the user account, the first identification information identifying the medical device; and
   receiving a message to delete the first identification information after the medical device fails to be provided to the user within a threshold period of time.

* * * * *